US011498894B2

(12) United States Patent
Stoutenburg et al.

(10) Patent No.: US 11,498,894 B2
(45) Date of Patent: Nov. 15, 2022

(54) INTEGRATED METHODS AND SYSTEMS FOR PRODUCING AMIDE AND NITRILE COMPOUNDS

(71) Applicant: Novomer, Inc., Rochester, NY (US)

(72) Inventors: Eric Stoutenburg, Rochester, NY (US); Utpal Mahendra Vakil, Evansville, IN (US); Yuan Yan, Rochester, NY (US); Sadesh H. Sookraj, Rochester, NY (US)

(73) Assignee: Novomer, Inc., Rochester, NY (US)

( * ) Notice: Subject to any disclaimer, the term of this patent is extended or adjusted under 35 U.S.C. 154(b) by 0 days.

(21) Appl. No.: 17/436,917

(22) PCT Filed: Feb. 28, 2020

(86) PCT No.: PCT/US2020/020317
§ 371 (c)(1),
(2) Date: Sep. 7, 2021

(87) PCT Pub. No.: WO2020/185420
PCT Pub. Date: Sep. 17, 2020

(65) Prior Publication Data
US 2022/0041546 A1  Feb. 10, 2022

Related U.S. Application Data

(60) Provisional application No. 62/815,993, filed on Mar. 8, 2019.

(51) Int. Cl.
*C07C 253/20* (2006.01)
*C07C 231/12* (2006.01)

(52) U.S. Cl.
CPC .......... *C07C 253/20* (2013.01); *C07C 231/12* (2013.01)

(58) Field of Classification Search
None
See application file for complete search history.

(56) References Cited

U.S. PATENT DOCUMENTS

| | | |
|---|---|---|
| 2,361,036 A | 10/1944 | Kung |
| 2,375,005 A | 5/1945 | Kung |
| 2,508,279 A | 5/1950 | Lichtenwalter et al. |
| 2,525,794 A | 10/1950 | Gresham |
| 2,548,155 A | 4/1951 | Gresham et al. |
| 2,691,643 A | 10/1954 | Chirtel |
| 3,128,163 A | 4/1964 | Weittenhiller et al. |
| 3,169,945 A | 2/1965 | Hostettler |
| 3,211,706 A | 10/1965 | Bomer |
| 3,471,451 A | 10/1969 | Moore |
| 3,525,718 A | 8/1970 | Derieg |
| 3,678,069 A | 7/1972 | Busier |
| 3,885,155 A | 5/1975 | Anbar |
| 3,954,854 A | 5/1976 | Gehrmann et al. |
| 4,230,885 A | 10/1980 | Wu |
| 4,317,926 A | 3/1982 | Sato et al. |
| 4,427,884 A | 1/1984 | Anbar et al. |
| 4,759,313 A | 7/1988 | Dye |
| 4,973,841 A | 11/1990 | Purser |
| 5,138,086 A | 8/1992 | Honda et al. |
| 5,310,948 A | 5/1994 | Drent et al. |
| 5,359,081 A | 10/1994 | Drent et al. |
| 5,438,194 A | 8/1995 | Koudijs et al. |
| 5,648,452 A | 7/1997 | Schechtman et al. |
| 5,661,299 A | 8/1997 | Purser |
| 5,705,688 A | 1/1998 | Fauconet et al. |
| 6,133,402 A | 10/2000 | Coates et al. |
| 6,252,110 B1 | 6/2001 | Uemura et al. |
| 6,316,590 B1 | 11/2001 | Coates et al. |
| 6,538,101 B2 | 3/2003 | Coates et al. |
| 6,541,665 B1 | 4/2003 | Bastiaensen et al. |
| 6,608,170 B1 | 8/2003 | Coates |
| 6,852,865 B2 | 2/2005 | Coates et al. |
| 6,887,380 B2 | 5/2005 | Lee et al. |
| 7,420,064 B2 | 9/2008 | Luinstra et al. |
| 8,246,915 B2 | 8/2012 | Boer et al. |
| 8,445,703 B2 | 5/2013 | Allen et al. |
| 8,796,475 B2 | 8/2014 | Allen et al. |
| 9,096,510 B2 | 8/2015 | Porcelli et al. |
| 9,115,070 B2 | 8/2015 | Pazicky et al. |
| 9,156,803 B2 | 10/2015 | Allen et al. |
| 9,206,144 B2 | 12/2015 | Allen et al. |
| 9,327,280 B2 | 5/2016 | Lee et al. |
| 9,403,788 B2 | 8/2016 | Lee et al. |
| 9,493,391 B2 | 11/2016 | Allen et al. |
| 9,738,784 B2 | 8/2017 | Allen et al. |
| 9,914,689 B2 | 3/2018 | Porcelli et al. |

(Continued)

FOREIGN PATENT DOCUMENTS

| | | |
|---|---|---|
| CN | 102421821 A | 4/2012 |
| CN | 104245657 A | 12/2014 |

(Continued)

OTHER PUBLICATIONS

Work, Stewart D. et al. "Condensations at the Methyl Groups of N-Acetylbenzamide and Diacetylimide by Means of Potassium Amide in Liquid Ammonia." Journal of the American Chemical Society, vol. 86, No. 5, Mar. 1, 1964, pp. 372-876.
Search Report for Taiwan Patent Application No. 107108981. Date of completion: Nov. 6, 2020.
Chinese Office Action for Application No. 201680055982.1 dated Jun. 1, 2020.
Abe et al., "Effects of Residual Zinc Compounds and Chain-End Structure on Thermal Degradation of Poly(?-caprolactone)". Biomacromolecules, vol. 5, 2004, pp. 1480-1488.
Abe, Hideki, "Thermal Degradation of Environmentally Degradable Poly(Hydroxyalkanoic Acid)s", Macromolecular Bioscience, vol. 6, 2006, pp. 469-486.
Agostini et al., "Synthesis and Characterization of Poly-?-Hydroxybutyrate. I. Synthesis of Crystalline DL-Poly-?-Hydroxybutyrate from DL-?-Butyrolactone", Journal of Polymer Science, Part A-1, vol. 9, No. 10, 1971, pp. 2775-2787.

(Continued)

*Primary Examiner* — Joseph R Kosack
(74) *Attorney, Agent, or Firm* — Young Basile Hanlon & MacFarlane, P.C.

(57) ABSTRACT

Provided herein are integrated methods and systems for the production of acrylamide and acrylonitrile compounds and other compounds from at least beta-lactones and/or beta-hydroxy amides.

20 Claims, 4 Drawing Sheets

(56) References Cited

U.S. PATENT DOCUMENTS

| | | |
|---|---|---|
| 10,065,914 B1 | 9/2018 | Ruhl et al. |
| 10,099,988 B2 | 10/2018 | Farmer et al. |
| 10,099,989 B2 | 10/2018 | Sookraj |
| 10,144,802 B2 | 12/2018 | Sookraj |
| 10,221,150 B2 | 3/2019 | Farmer et al. |
| 10,221,278 B2 | 3/2019 | Lee et al. |
| 10,245,559 B2 | 4/2019 | Lapointe et al. |
| 10,597,294 B2 | 3/2020 | Sookraj |
| 10,626,073 B2 | 4/2020 | Farmer |
| 10,738,022 B2 | 8/2020 | Farmer |
| 10,829,372 B2 | 11/2020 | Sookraj |
| 10,927,091 B2 | 2/2021 | Farmer |
| 2002/0028909 A1 | 3/2002 | Kelsey et al. |
| 2005/0014977 A1 | 1/2005 | Drent et al. |
| 2007/0161806 A1 | 7/2007 | Preishuber-Pflugl et al. |
| 2007/0219397 A1 | 9/2007 | Holladay et al. |
| 2009/0246430 A1 | 10/2009 | Kriegel et al. |
| 2011/0262669 A1 | 10/2011 | Kriegel et al. |
| 2012/0123137 A1 | 5/2012 | Allen et al. |
| 2013/0165670 A1 | 6/2013 | Allen et al. |
| 2013/0209775 A1 | 8/2013 | Allen et al. |
| 2013/0281715 A1 | 10/2013 | Allen et al. |
| 2014/0018574 A1 | 1/2014 | Raith et al. |
| 2014/0197580 A1 | 7/2014 | Poulat |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0126772 A1 | 5/2015 | Cao et al. |
| 2015/0141693 A1 | 5/2015 | Allen et al. |
| 2015/0183708 A1 | 7/2015 | Harris et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0288057 A1 | 10/2016 | Lapointe et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0153746 A1 | 6/2018 | Sookraj |
| 2018/0155490 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0305289 A1 | 10/2018 | Sookraj et al. |
| 2018/0354882 A1 | 12/2018 | Sookraj |
| 2019/0002293 A1 | 1/2019 | Sookraj et al. |
| 2019/0002385 A1 | 1/2019 | Sookraj et al. |
| 2019/0030520 A1 | 1/2019 | Lee |
| 2019/0031592 A1 | 1/2019 | Sookraj et al. |
| 2019/0047972 A1 | 2/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |
| 2020/0247742 A1 | 8/2020 | Farmer |

FOREIGN PATENT DOCUMENTS

| | | |
|---|---|---|
| EP | 0887334 A1 | 12/1998 |
| JP | 2003137850 A | 5/2003 |
| JP | 4356292 B2 | 11/2009 |
| JP | 45-19281 B2 | 8/2010 |
| SU | 1169528 A3 | 7/1985 |
| WO | 2003018540 A1 | 3/2003 |
| WO | 2009/155086 A2 | 12/2009 |
| WO | 2010/118128 A1 | 10/2010 |
| WO | 2011/100608 A1 | 8/2011 |
| WO | 2012/030619 A1 | 3/2012 |
| WO | 2012/051219 A2 | 4/2012 |
| WO | 2012/158573 A1 | 11/2012 |
| WO | 2013/063191 A1 | 5/2013 |
| WO | 2013/122905 A1 | 8/2013 |
| WO | 2013/126375 A1 | 8/2013 |
| WO | 2013/185009 A1 | 12/2013 |
| WO | 2014/004858 A1 | 1/2014 |
| WO | 2014/008232 A2 | 1/2014 |
| WO | 2015/085295 A2 | 6/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165323 A1 | 9/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/106824 A1 | 6/2018 |
| WO | 2018/107185 A1 | 6/2018 |
| WO | 2018/136638 A1 | 7/2018 |
| WO | 2018/144998 A1 | 8/2018 |
| WO | 2018/170006 A1 | 9/2018 |
| WO | 2018/200466 A1 | 11/2018 |
| WO | 2018/200471 A1 | 11/2018 |
| WO | 2019/006366 A1 | 1/2019 |
| WO | 2019/006377 A1 | 1/2019 |
| WO | 2019/050649 A1 | 3/2019 |
| WO | 2019/051184 A1 | 3/2019 |
| WO | 2019/070981 A1 | 4/2019 |

OTHER PUBLICATIONS

"Beta Elimination of Esters in Poly Lactones", Aug. 17, 2017, 1 page.

Billingham et al., "Polymerization and Copolymerization of ?-Butyrolactone by Aluminium Compounds", Journal of Organometallic Chemistry, vol. 341, No. 1-3, 1988, pp. 83-93.

Church et al., "Carbonylation of Heterocycles by Homogeneous Catalysts", Chemical Communications, vol. 21, No. 7, 2007, pp. 657-674.

Collias et al., "Biobased Terephthalic Acid Technologies: A Literature Review", Industrial Biotechnology, vol. 10, No. 2, Apr. 2014, pp. 91-105.

Dunn, Erin Whitfield., "Synthesis of Poly(Hydroxyalkanoates): Routes to Poly(3-Hydroxybutyrate) and Poly(3-Hydroxypropionate) from the Carbonylation and Ring-Opening Polymerization of Epoxides", A Dissertation Presented to the Faculty of the Graduate School of Cornell University, Aug. 2012, pp. 1-139.

Garozzo et al., "Primary Thermal Decomposition Processes in Aliphatic Polyesters Investigated by Chemical Ionization Mass Spectrometry", Macromolecules, vol. 19, No. 6, 1986, pp. 1643-1649.

Getzler et al., "Catalytic Carbonylation of ?-Lactones to Succinic Anhydrides", Journal of the American Chemical Society, vol. 126, No. 22, 2004, pp. 6842-6843.

Gresham et al., "?-Propiolactone I. Polymerization Reactions", J. Am. Chem. Soc., vol. 70, Mar. 1948, pp. 398-999.

(56) References Cited

OTHER PUBLICATIONS

Gresham et al., "?-Propiolactone II. Reactions with Salts of Inorganic Acids", J. Am. Chem. Soc., vol. 70, Mar. 1948, pp. 999-1001.
Gresham et al., "?-Propiolactone III. Reactions with Dithiocarbamic Acids, their Salts and Thiourea", J. Am. Chem. Soc., vol. 70, Mar. 1948, pp. 1001-1002.
Gresham et al., "?-Propiolactone IV. Reactions with Salts of Carboxylic Acids", J. Am. Chem. Soc., vol. 70, Mar. 1948, pp. 1003-1004.
Gresham et al., "?-Propiolactone V. Reaction with Alcohols", J. Am. Chem. Soc., vol. 70, Mar. 1948, pp. 1004-1006.
Gross et al., "Polymerization of ?-Monosubstituted-?-Propiolactones using Trialkylaluminum-Water Catalytic Systems and Polymer Characterization", Macromolecules, vol. 21, No. 9, 1988, pp. 2657-2668.
Hori et al., "Ring-Opening Polymerization of Optically Active ?-Butyrolactone using Distannoxane Catalysts: Synthesis of High-Molecular-Weight Poly(3-Hydroxybutyrate)", Macromolecules, vol. 26, No. 20, 1993, pp. 5533-5534.
International Preliminary Report on Patentability received for PCT Patent Application No. PCT/US2016/044772, dated Feb. 15, 2018, 13 pages.
International Preliminary Report on Patentability received for PCT Patent Application No. PCT/US2016/044927, dated Feb. 15, 2018, 13 pages.
International Search Report and Written Opinion received for PCT Patent Application No. PCT/US2016/044772, dated Nov. 8, 2016, 17 pages.
International Search Report and Written Opinion received for PCT Patent Application No. PCT/US2016/044927, dated Nov. 8, 2016, 17 pages.
Wabuchi et al., "The Thermal Degradation of Poly(Oxycarbonylethylene) (Poly-?-Propiolactone)", Die Makromolekulare Chemie, vol. 165, 1973, pp. 59-72.
Jacobi et al., "Strukturuntersuchung von Polyestern durch direkten Abbau im Massenspektrometer, 4. Polyester und Copolyester der Milcäure und Glykolsäure", Macromolecular Chemistry and Physics, vol. 179, 1978, pp. 429-436 (with English Abstract).
Kim et al., "Effect of Metal Compounds on Thermal Degradation Behavior of Aliphatic Poly(Hydroxyalkanoic Acid)s", Polymer Degradation and Stability, vol. 93, 2008, pp. 776-785.
Kim et al., "Effects of Residual Metal Compounds and Chain-End Structure on Thermal Degradation of Poly(3-Hydroxybutyric Acid)", Polymer Degradation and Stability, vol. 91, 2006, pp. 769-777.
Kim et al., "Thermal Degradation Behavior of Poly(4-Hydroxybutyric Acid)", Polymer Degradation and Stability, vol. 91, 2006, pp. 2333-2341.
Kopinke et al., "Thermal Decomposition of Biodegradable Polyesters-I: Poly(?-Hydroxybutyric Acid)", Polymer Degradation and Stability, vol. 52, 1996, pp. 25-38.
Kricheldorf et al., "Strukturuntersuchung von Polyestern durch direkten Abbau im Massenspektrometer, 3. Poly-?-Propiolacton, poly-?-Pivalolacton und poly-?-Valerolacton", Macromolecular Chemistry and Physics, vol. 179, 1978, pp. 421-427 (with English Abstract).
Liu et al., "Reducing the Formation of Six-Membered Ring Ester during Thermal Degradation of Biodegradable PHBV to Enhance its Thermal Stability", Polymer Degradation and Stability, vol. 94, 2009, pp. 18-24.

Luderwald et al., "Strukturuntersuchung von Polyestern durch direkten Abbau im Massenspektrometer, 2. Aliphatische Polyester", 2. Makromol. Chem. vol. 177, 1976, pp. 2093-2111 (with English Abstract).
Mahmoud et al., "Production of Benzoic Acid from Biomass-Derived Furan and Methyl Acrylate Using Lewis-Acidic Zeolites", Catalysis at the Confluence of Science and Technology, Jun. 15, 2015, pp. 1-2.
Nguyen et al., "Thermal Degradation of Poly(3-Hydroxyalkanoates): Preparation of Well-Defined Oligomers", Biomacromolecules, vol. 3, 2002, pp. 219-224.
Rieth et al., "Single-Site ?-Diiminate Zinc Catalysts for the Ring-Opening Polymerization of ?-Butyrolactone and ?-Valerolactone to Poly(3-Hydroxyalkanoates)", Journal of the American Chemical Society, vol. 124, No. 51, 2002, pp. 15239-15248.
Schechtman et al., "Chemical Synthesis of Isotactic Poly(3-Hydroxyalkanoates)", Polymer Preprints, Division of Polymer Chemistry, Inc., vol. 40, No. 1, 1999, pp. 508-509.
Slowik et al., "Catalytic Conversion of Waste Carbon Monoxide to Valuable Chemicals & Materials", Technical Proceedings of the Clean Technology Conference and Trade Show, 2010, pp. 283-286.
Smith et al., "March's Advanced Organic Chemistry: Reactions, Mechanisms and Structure", Sixth Edition, A John Wiley & Sons, Inc., 2007, 2374 pages.
Sorrell, Thomas N., "Organic Chemistry", Second Edition, University Science Books, 1999, 24 pages.
Tachibana et al., "Synthesis and Verification of Biobased Terephthalic Acid from Furfural", Scientific Reports, vol. 5, No. 8249, 2015, pp. 1-5.
Tanahashi et al., "Thermal Properties and Stereoregularity of Poly (3-Hydroxybutyrate) Prepared from Optically Active ?-Butyrolactone with a Zinc-based Catalyst", Macromolecules, vol. 24, No. 20, 1991, pp. 5732-5733.
Varma?Nair et al., "Heat Capacity and other Thermodynamic Properties of Linear Macromolecules: X. Update of the ATHAS 1980 Data Bank", Journal of Physical and Chemical Reference Data, vol. 20, No. 2, 1991, pp. 349, 375 & 400.
Vera et al., "Synthesis and Crystal Structure of Dimethyl-7-oxabicyclo[2.2.1]hept-5-ene exo,exo-2,3-dicarboxylate", Journal of Chemical Crystallography, vol. 37, 2007, pp. 543-548.
Zhang et al., "Stereochemistry of the Ring-Opening Polymerization of (S)-?-Butyrolactone", Macromolecules, vol. 23, No. 13, 1990, pp. 3206-3212.
Zhu et al., "Polymorphic Crystallization and Melting-Recrystallization Behavior of Poly(3-Hydroxypropionate)", Macromolecules, vol. 38, 2005, pp. 6455-6465.
Steunenberg, Peter et al., "Polymerisation of b-alanine through catalytic ester-amide exchange", European Polymer Journal, Pergamon Press Ltd. Oxford, GB, vol. 49, No. 7, Apr. 9, 2013, pp. 1773-1781.
Extended European Search Report for co-pending European Application EP 18 76 8532 dated Dec. 2, 2020 (9 pages).
Office Action (and English translation) issued in co-pending application JP 2020-513756 dated Feb. 19, 2021. 16 page.
Gresham, T.L. et al. "Reactions With Ammonia and Amines." Journal of the American Chemical Society, 1951, 73, 7, 3168-3171.
International Preliminary Report on Patentability for co-pending PCT/US2018/022248 dated Apr. 21, 2018 (7 pages).
International Search Report and Written Opinion for co-pending PCT/US2018/022248 US2018/022248 dated May 24, 2018 (9 pages).
International Search Report and Written Opinion for co-pending PCT/US2020/020317 dated Jul. 14, 2020. (15 pages).

INTEGRATED METHODS AND SYSTEMS FOR PRODUCING AMIDE AND NITRILE COMPOUNDS

CROSS-REFERENCE TO RELATED APPLICATION(S)

This application is a 371 application of International Application No. PCT/US2020/020317, filed on Feb. 28, 2020, which claims priority from U.S. Provisional Application No. 62/815,993, filed Mar. 8, 2019, the entire disclosure of which is hereby incorporated by reference.

The present disclosure relates generally to the production of amide products and/or nitrile products, and more specifically from at least epoxides, beta-lactones and/or beta-hydroxy amides.

BACKGROUND

Nitrogen containing compounds such as amides and nitriles are valuable compounds that can be used for various commercial and Industrial applications. For example, acrylonitrile may be used as a starting material in the production of polymers and monomer precursors. Various methods for the industrial production of acrylonitrile are known in the art. For example, acrylonitrile can be prepared by the catalytic ammoxidation of propylene, in which propylene, ammonia and air are contacted with a catalyst at elevated temperature and pressure. This process, however, generally requires the use of harsh reaction conditions and costly reagents.

There remains a need in the art for the development of integrated methods and systems for the industrial production of nitriles, and nitrile precursors, that employ inexpensive and renewable feed stocks, are designed to consolidate multiple synthetic operations and avoid costly purification of intermediates, and allow for the production of nitriles, and nitrile precursors, under mild reaction conditions.

BRIEF SUMMARY

Disclosed are integrated methods and systems for the industrial production of nitriles, and nitrile precursors, and other compounds desired in the art, including methods and systems of producing such compounds, either in part or completely, from renewable sources.

Disclosed is a method comprising: combining a hydroxypropanamide stream comprising a hydroxypropanamide with a dehydration agent to produce a product stream comprising an unsaturated amide and/or an unsaturated nitrile, or isomers thereof. Disclosed is a method of producing amide products and/or nitrile products by combining a hydroxypropanamide stream with dehydration agent. The hydroxypropanamide may be combined with the dehydration agent in the presence of a solvent and ammonia. The hydroxypropanamide may be combined with the dehydration agent in the presence of a solvent and ammonia. Disclosed is a method comprising combining the beta lactone with ammonia in a solvent. The ammonia may be added to the beta lactone at a temperature of about −100° G to less than 100° G. The combining of the beta lactone with ammonia may be isothermally controlled. The beta lactone may be prepared by contacting carbon monoxide with an epoxide in the presence of a carbonylation catalyst. Contacting carbon monoxide with an epoxide in the presence of a carbonylation catalyst may produce a carbonylation product stream comprising the beta lactone. The method may comprise distilling the product stream comprising the unsaturated amide and/or the unsaturated nitrile, or isomers thereof, to isolate the unsaturated amide and/or the unsaturated nitrile. The hydroxypropanamide stream may comprise molten hydroxypropanamide, and optionally a carrier gas. The dehydration agent may be heterogeneous, The hydroxypropanamide stream may be contacted with the heterogeneous dehydration agent to produce a product stream comprising the unsaturated amide and/or the unsaturated nitrile, or isomers thereof. Any one of the disclosed steps may be performed in the solvent of a polar aprotic solvent, an alcohol, or a combination thereof. The beta lactone may be contacted with anhydrous ammonia at a temperature of from −100° C. to 35° C. to prepare the hydroxypropanamide. The beta lactone and the anhydrous ammonia may be contacted in a solvent. The beta lactone and the anhydrous ammonia may be contacted in the presence of a base. The dehydration agent may comprise $TiO_2$ or $SiO_2$, or a combination thereof. The dehydration agent may comprises $TiO_2$ and $SiO_2$. The dehydration agent may be provided in a column, and the column have a zone comprising the $TiO_2$ and a separate zone comprising the $SiO_2$. The zone comprising the $TiO_2$ may operate at a first temperature, and the zone comprising the $SiO_2$ may operate at a second temperature, wherein the first temperature and second temperature are different.

The hydroxypropanamide stream may be produced by combining a mixed feed stream with ammonia. The beta lactone may be produced by carbonylating epoxide with carbon monoxide in the presence of carbonylation catalyst and solvent to produce a carbonylation product stream comprising beta lactone, solvent, and carbonylation catalyst. The beta lactone and the anhydrous ammonia are contacted in the presence of a base. The carbonylation catalyst may be separated from the carbonylation product stream to produce the mixed feed stream. Disclosed is a method of producing a hydroxypropanamide stream by combining a mixed feed stream with ammonia. The hydroxypropanamide stream may be produced by combining beta lactone with anhydrous ammonia at a temperature between −100° C. and less than 100° C., between −75° C. and 70° C. or between −100 and 35° C. The hydroxypropanamide stream may be prepared by combining a mixed feed stream with anhydrous ammonia at a temperature between −100° C. and less than 100° C., or between −75° C. and 70° C. In another aspect, provided is a method of producing a hydroxypropanamide stream by combining a mixed feed stream with anhydrous ammonia at a temperature between −100° C. and 35° C. Provided is a method of producing amide products and/or nitrile products by combining a mixed feed stream with ammonia and a dehydration agent. The hydroxypropanamide stream may comprise hydroxypropanamide, solvent and ammonia. The mixed feed stream may comprise beta lactone and solvent. Provided is a method of producing amide products and/or nitrile products by contacting a hydroxypropanamide stream over a heterogeneous dehydration agent, wherein the hydroxypropanamide stream comprises molten hydroxypropanamide and carrier gas. Provided is a system comprising a reactor that receives a mixed feed stream and ammonia; and outputs a hydroxypropanamide stream.

Provided is a system comprising a reactor configured to produce a product stream in the presence of dehydration agent, wherein the product stream comprises amide products and/or nitrile products, the solvent, and ammonia. The reactor may receive a hydroxypropanamide stream; and outputs the product stream. The reactor may receive a mixed feed stream and ammonia; and outputs the product stream. The hydroxypropanamide stream may comprises hydroxypropanamide, solvent and ammonia. The mixed feed stream may comprise beta lactone and solvent.

The beta lactone may corresponds to formula (1)

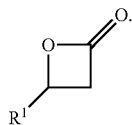

The hydroxypropanamide may correspond to formula (2)

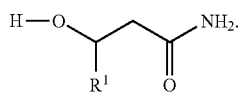

The unsaturated nitrile corresponds to formula (3)

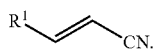

The unsaturated amide corresponds to formula (3-I)

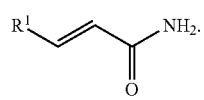

The epoxide may correspond to formula (E)

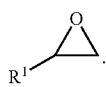

In these formulas $R^1$ is H, alkyl, alkenyl, cycloalkyl or aryl; or, H or alkyl.

Disclosed is a method comprising: preparing an unsaturated amide or unsaturated nitrile, or isomers thereof, as disclosed herein and polymerizing the unsaturated amide or unsaturated nitrile, or isomers thereof.

Disclosed is a system, comprising: a reactor, comprising: at least one inlet configured to receive (i) a mixed feed stream comprising a beta lactone and solvent and (li) ammonia; and an outlet configured to release a hydroxypropanamide stream comprising a hydroxypropanamide, solvent, and ammonia. The disclosed system may comprise an additional reactor configured to receive the hydroxypropanamide stream and to produce a product stream in the presence of dehydration agent, wherein the product stream comprises an unsaturated amide and/or an unsaturated nitrile, or isomers thereof, the solvent, and ammonia. The additional reactor may comprise a multitemperature stage column. The system may comprise comprising a distillation unit configured to collect: i) the unsaturated amide and/or the unsaturated nitrile, or isomers thereof; ii) the solvent; or iii) ammonia; or iv) any combination of the above i)-iii).

Disclosed is a system comprising: a reactor configured to produce a product stream in the presence of dehydration agent, wherein the reactor comprises: an inlet configured to receive a hydroxypropanamide stream comprising a hydroxypropanamide, solvent, and ammonia, wherein: and an outlet configured to output the product stream, wherein the product stream comprises the unsaturated amide and/or the unsaturated nitrile, or isomers thereof, the solvent, and ammonia.

Disclosed is a reactor configured to produce a product stream in the presence of dehydration agent, wherein the reactor comprises: at least one inlet configured to receive (i) a mixed feed stream comprising a compound of beta lactone and solvent, and (ii) ammonia; and an outlet configured to output the product stream, comprising an unsaturated amide and/or an unsaturated nitrile, or isomers thereof, the solvent, and ammonia. The reactor may comprise a multitemperature stage column.

DESCRIPTION OF THE FIGURES

The present application can be best understood by reference to the following description taken in conjunction with the accompanying figures, in which like parts may be referred to by like numerals.

DETAILED DESCRIPTION

The following description sets forth exemplary methods, parameters and the like, it should be recognized, however, that such description is not intended as a limitation on the scope of the present disclosure but is instead provided as a description of exemplary embodiments.

Provided herein are integrated methods and systems for the production of amide products and/or nitrile products, as well as precursors of such products, in certain embodiments, the amide products include acrylamide, and the nitrile products include acrylonitrile. In some variations, the amide product is a compound corresponding to formula (3-I), and the nitrile product is a compound corresponding to the formula (3), or isomers thereof, wherein $R^1$ is H or alkyl:

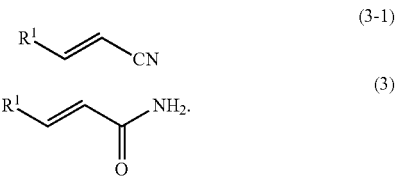

Integrated Methods

In some aspects, provided is an integrated method of producing amide products and/or nitrile products, and precursors thereof.

The integrated methods are disclosed in the following process flow diagrams.

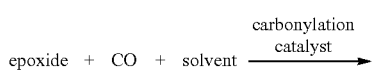

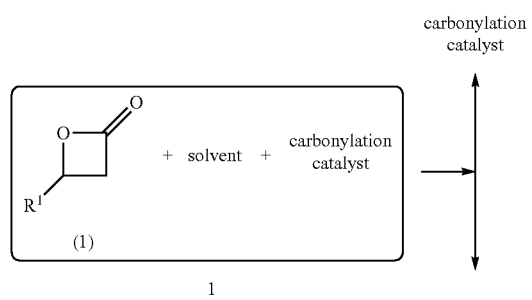

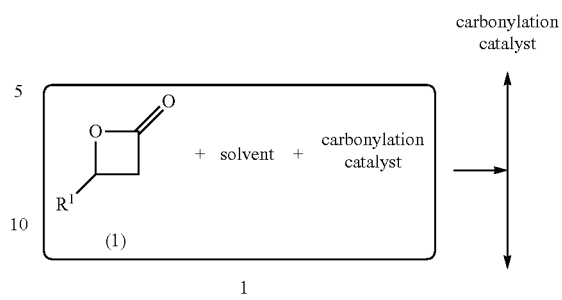

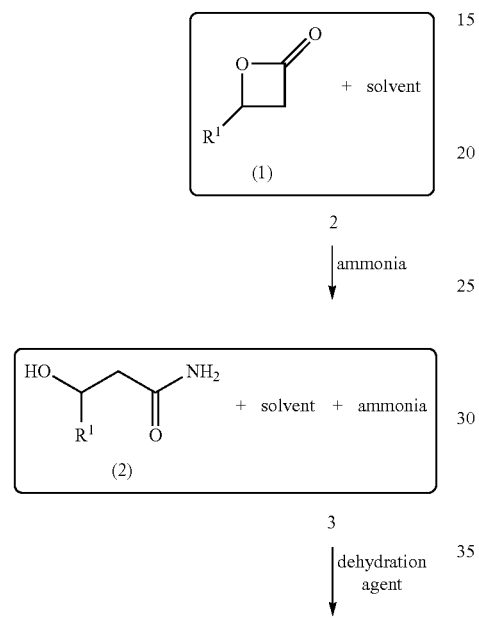

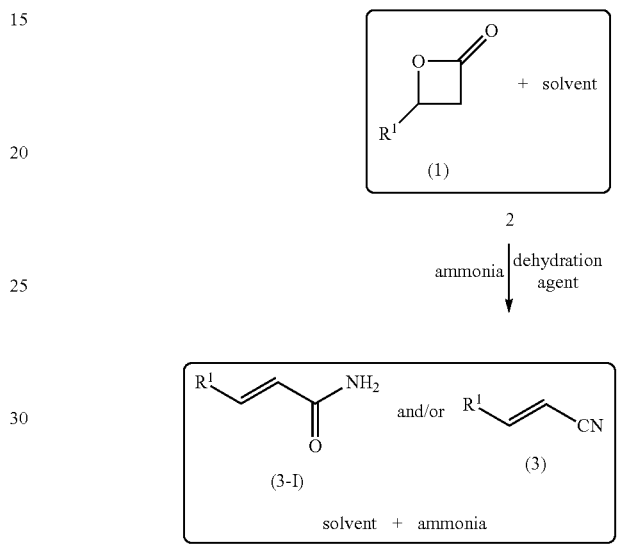

Disclosed is another process flow diagram.

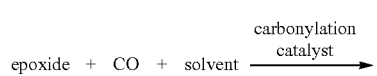

In certain embodiments, the amide products and/or nitrile products may be derived from epoxide and carbon monoxide. For example, in some variations, the epoxide is a compound of formula (E):

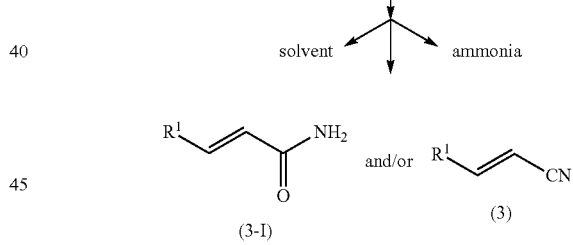

wherein $R^1$ is as defined above for formulae (3-I) and (3).

Figure 1:
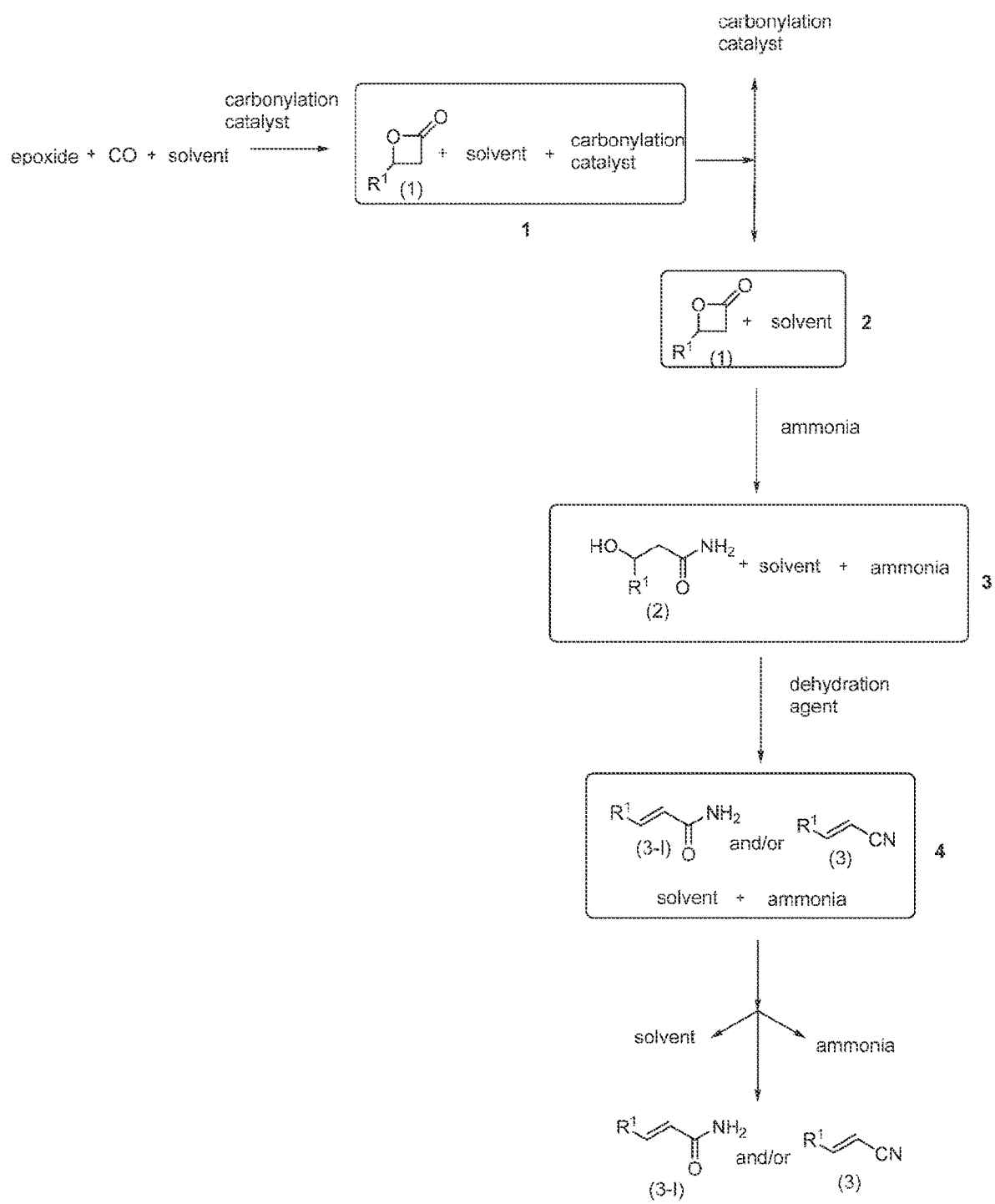
FIGS. 1 and 2 depict exemplary process for the integrated production of amide products and/or nitrile products of formulae (3) and (3-I).

With reference to FIG. 1, an exemplary reaction scheme to produce a compound of formula (3-I) and/or a compound of formula (3), or isomers thereof, from epoxide and carbon monoxide is depicted. Epoxide undergoes carbonylation to produce beta lactone, such as a compound of formula (1):

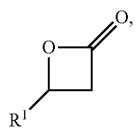

(1)

wherein R¹ is as defined hereinbefore.

Such carbonylation reaction takes place in the presence of carbonylation catalyst and solvent to produce carbonylation product stream 1, which includes the compound of formula (1), solvent and carbonylation catalyst. Carbonylation product stream 1 may undergo further processing steps to remove carbonylation catalyst. As depicted in FIG. 1, carbonylation product stream 1 undergoes a separation step to remove carbonylation catalyst from the stream, yielding mixed feed stream 2, which comprises the compound of formula (1) and solvent. Any suitable techniques may be employed to separate carbonylation catalyst from carbonylation product stream 1. For example, in some variations, a membrane, such as a nanofiltration membrane, may be used. Without requiring further processing of mixed feed stream 2 to remove solvent, mixed feed stream 2 is combined with ammonia to produce hydroxypropanamide stream 3, which comprises a compound of formula (2), solvent and ammonia. Ammonia may be provided at any suitable temperatures to convert the compound of formula (1) in mixed feed stream 2 to the compound of formula (2) in hydroxypropanamide stream 3. In some variations of the foregoing, the ammonia is provided at a temperature between −100° G to about less than 100° C., between −100° C. to about 70° C., between −100° C. to about 35° C., between −100° G to about 0° C., between −100° C. to about −20° G, between −100° C. to about −50° C., between −100° G to about 10° G, between −100° C. to about 0° C., −100° C. to about −20° G, or between −100° C. to about −50° C.

In some variations, mixed feed stream 2 is added to the ammonia to produce the hydroxypropanamide stream 3, in one variation, the mixed feed stream is added to excess ammonia. In certain variations, the mixed feed stream is added to the ammonia over the course of 60 minutes to 1 minute, or 30 minutes to 5 minutes, 30 minutes to about 15 minutes, or 15 minutes to 5 minutes; or about 60 minutes, about 30 minutes, about 15 minutes, or about 5 minutes, in some embodiments, the mixed feed stream is added to the ammonia at any rate suitable to maintain a constant temperature. In other variations, the combining of mixed feed stream 2 with ammonia is isothermally controlled. By controlling the reaction conditions of this step, the reaction may be driven to selectively produce the compound of formula (2). For example, in some variations, the method comprises combining mixed feed stream 2 with anhydrous ammonia at a temperature between −100° C. and 35° C. to produce hydroxypropanamide stream 3, in certain variations of the foregoing, the compound of formula (2) present in hydroxypropanamide stream 3 is produced with a selectivity of greater than 50%, greater than 60%, greater than 70%, greater than 80%, or greater than 90%.

Hydroxypropanamide can then undergo dehydration to produce the amide products and/or nitrile products. With again reference to FIG. 1, hydroxypropanamide stream 3 is combined with dehydration agent to produce product stream 4, which comprises the compound of formula (3-I) and/or the compound of formula (3), or isomers thereof, as well as solvent and ammonia. It should be understood that, in some variations as depicted in FIG. 1, hydroxypropanamide stream 3 does not require further processing to remove solvent and/or ammonia at this stage. Rather, solvent and/or ammonia may be carried through the integrated process and removed after production of product stream 4. With reference again to FIG. 1, product stream 4 undergoes a separation step to isolate the compound of formula (3-I), the compound of formula (3), or isomers thereof, solvent and/or ammonia.

Thus, in some aspects, provided is an integrated method comprising: carbonylating an epoxide feed stream comprising a compound of formula (E-I), in the presence of carbonylation catalyst and solvent to produce a carbonylation product stream comprising a compound of formula (1), solvent, and carbonylation catalyst; separating carbonylation catalyst from the carbonylation product stream to produce a mixed feed stream comprising the compound of formula (1) and solvent; combining the mixed feed stream with ammonia to produce a hydroxypropanamide stream comprising a compound of formula (2), solvent and ammonia; and combining the hydroxypropanamide stream with dehydration agent to produce a product stream comprising the compound of formula (3-I) and/or the compound of formula (3), or isomers thereof, solvent, and ammonia.

Although FIG. 1 depicts an exemplary reaction scheme that involves a separation step to isolate carbonylation catalyst from the carbonylation product stream, in other variations where heterogeneous carbonylation catalyst is used, such separation step may not be required. For example, in other aspects, the method comprises: carbonylating an epoxide feed stream comprising a compound of formula (E-I), in the presence of heterogeneous carbonylation catalyst and solvent to produce a mixed feed stream comprising a compound of formula (1) and solvent; combining the mixed feed stream with ammonia to produce the hydroxypropanamide stream comprising a compound of formula (2), solvent and ammonia; and combining the hydroxypropanamide stream with dehydration agent to produce a product stream comprising the compound of formula (3-I) and/or the compound of formula (3), or isomers thereof, the solvent, and ammonia. The resulting product stream may undergo further purification to isolate one or more components in the product stream, including isolating the compound of formula (3-I) and/or the compound of formula (3), or Isomers thereof. With reference again to FIG. 1, product stream 4 may undergo distillation to isolate one or more of: (a) the compound of formula (3-I) and/or the compound of formula (3), or isomers thereof; (b) solvent; and (c) ammonia. Although FIG. 1 depicts an exemplary reaction scheme to produce amide products and/or nitrile products from epoxide and carbon monoxide, it should be understood that in other variations, the compound of formula (1) and/or the compound of formula (2) may be obtained from commercially available sources.

Other variations of the exemplary reaction scheme depicted in FIG. 1 are also contemplated. For example, with reference to FIG. 2, mixed feed stream 2 may be combined with ammonia and dehydration agent in one step to produce product stream 4. In other variations, carrier gas may be used in the conversion of hydroxypropanamide to amide products and/or nitrile products. Thus, in certain aspects, provided is a method of producing a compound of formula (3-I) and/or a compound of formula (3), or isomers thereof, comprising: combining a hydroxypropanamide stream with carrier gas and dehydration agent to produce a product stream comprising the compound of formula (3-I) and/or the compound of formula (3), or isomers thereof. In some variations, the carrier gas comprises ammonia. In other variations, the carrier gas comprises ammonia and nitrogen, in some variations, the product stream further comprises ammonia, water, or a combination thereof.

The hydroxypropanamide may also be present in different forms in the integrated methods described herein. For example, in another variation, the method comprises combining molten compound of formula (2) and carrier gas with heterogeneous dehydration agent to produce the product stream comprising the compound of formula (3-I) and/or the compound of formula (3), or isomers thereof, as well as solvent. In some variations of the foregoing, with respect to formulae (1), (2), (3-I) and (3), $R^1$ is H. Thus, in one variation when $R^1$ is H, acrylonitrile is produced from beta-propiolactone, through 3-hydroxypropanamide and acrylamide. In other variations, $R^1$ is C1-10 alkyl. In another variation, $R^1$ is methyl.

In one example, a mixed feed stream comprising beta-propiolactone and solvent may be reacted with anhydrous ammonia to produce a hydroxypropanamide stream comprising 3-hydroxypropanamide, the solvent, and excess ammonia. Then, the hydroxypropanamide stream may be continuously fed to a fixed bed reactor which is packed with dehydration agent. In some variations, the hydroxypropanamide stream may be vaporized and mixed with a carrier gas before passing through the dehydration agent (e.g., in a catalyst bed) to produce a product stream comprising acrylonitrile, the solvent and ammonia. The product stream may be treated in order to isolate acrylonitrile, the solvent, and ammonia. in another example, beta-propiolactone may be reacted with anhydrous ammonia to produce 3-hydroxypropanamide. Then, neat 3-hydroxypropanamide may be continuously fed to a fixed bed reactor which is packed with dehydration agent. The 3-hydroxypropanamide solid may be warmed above its melting point, thus producing molten 3-hydroxypropanamide, and then further mixed/vaporized with nitrogen carrier gas in the preheat zone before passing through the dehydration agent (e.g., in a catalyst bed).

The amide products and/or nitrile products produced according to the methods and systems described herein may have uses in various downstream processes. For example, in one variation, acrylamide may be polymerized to form polyacrylamide; and acrylonitrile may be polymerized to form polyacrylonitrile. The resulting polyacrylonitrile may be suitable for various uses, including as carbon fiber. In some embodiments, provided are methods of producing a polymer, comprising producing a compound of formula (3-I) and/or a compound of formula (3), or isomers thereof, according to any of the methods described herein; and polymerizing the compound of formula (3-I) and/or the compound of formula (3), or isomers thereof.

Integrated Systems

In other aspects, provided herein are also systems for the integrated production of amide products and/or nitrile products, and precursors thereof. As described above for the integrated methods, the amide products and/or nitrile products may be derived from epoxide and carbon monoxide, in some variations, the epoxide is a compound of formula (E), and the other products produced therefrom may include beta lactones (such as a compound of formula (1)), hydroxypropanamides (such as a compound of formula (2), as well as the amide and nitrile products (such as compounds of formulae (3-I) and (3)).

Figure 3:
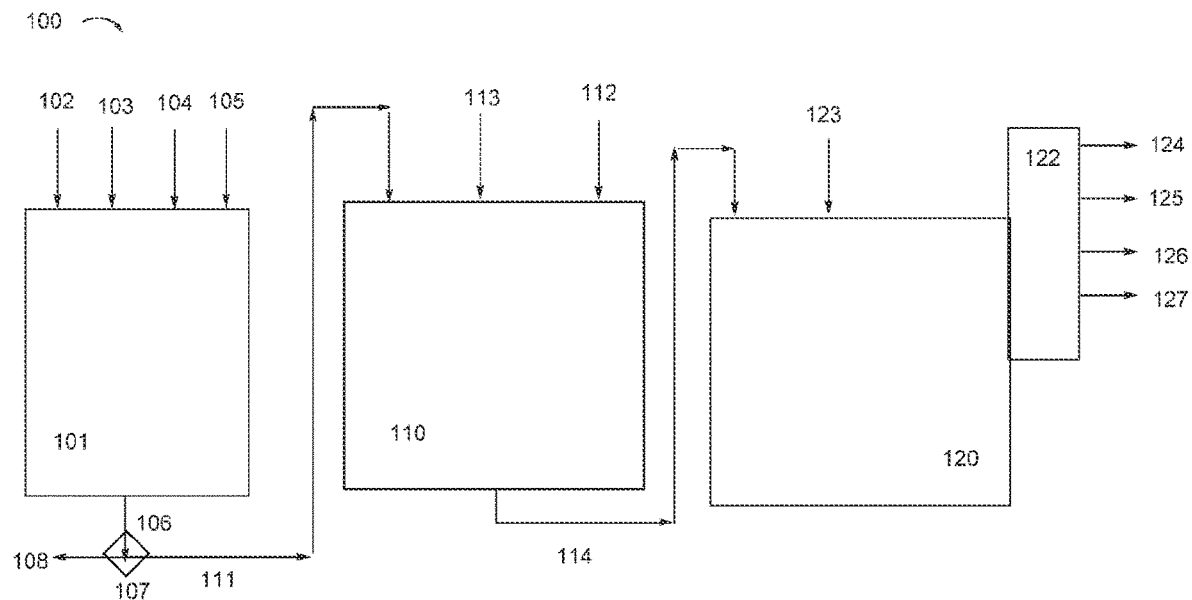
FIGS. 3, 4 and 5 depict exemplary systems for the Integrated production of amide products and/or nitrile products of formulae (3) and (3-I).

With reference to FIG. 3, system 100 is an exemplary system to produce a compound of formula (3-I) and/or a compound of formula (3), or isomers thereof, from epoxide and carbon monoxide. The carbonylation of epoxide takes place in reactor 101. Epoxide 102, carbon monoxide 103, solvent 104 and carbonylation catalyst 105 are fed into reactor 101. Epoxide is carbonylation in the presence of carbonylation catalyst and solvent to produce carbonylation product stream 106, which includes the compound of formula (1), solvent and carbonylation catalyst. Carbonylation product stream 106 may undergo further processing steps to remove carbonylation catalyst. As depicted in FIG. 3, carbonylation product stream 106 is directed to a separation unit 107, which separates carbonylation catalyst 108 and yields mixed feed stream 111, which comprises the compound of formula (1) and solvent. For example, in some variations, separation unit 107 may be a membrane, such as a nanofiltration membrane. Recovered carbonylation catalyst 108 may be reused and recycled back into system 100. Without requiring further processing of mixed feed stream 111 to remove solvent, mixed feed stream 111 is fed into reactor 110. Reactor 110 also receives ammonia 112 and optionally base 113. The compound of formula (1) in mixed feed stream 111 is converted to hydroxypropanamide, and reactor 110 outputs hydroxypropanamide stream 114, which comprises the compound of formula (2), solvent and ammonia, as well as base if used. The integrated system may be configured to provide ammonia 112 to reactor 110 at any suitable temperatures to convert the compound of formula (1) in mixed feed stream 111 to the compound of formula (2) in hydroxypropanamide stream 114, in some variations of the foregoing, system may be configured to provide ammonia at a temperature between −100° C. to about 35° C., between −100° C. to about 10° C., between −100° C. to about 0° G, between −100° C. to about −20° C., between −100° C. to about −50° C., between −100° C. to about 10° C., between −100° C. to about 0° C., −100° C. to about −20° C., or between −100° C. to about −50° C. in some variations, the system is configured to add mixed feed stream 111 to ammonia 112 in reactor 110 to produce hydroxypropanamide stream 114. In some variations, the mixed feed stream is added to an excess of ammonia in the reactor, in certain variations, the system is configured to add the mixed feed stream to the ammonia over the course of 60 minutes to 1 minute, or 30 minutes to 5 minutes, 30 minutes to about 15 minutes, or 15 minutes to 5 minutes; or about 60 minutes, about 30 minutes, about 15 minutes, or about 5 minutes. In some embodiments, the system is configured to add the mixed feed stream to the ammonia at any rate suitable to maintain a constant temperature, in some variations, reactor 110 is configured to receive ammonia 112 in liquid form. In other variations, reactor 110 is configured to receive mixed feed stream 111 in atomized form. In some variations of the foregoing, the reactor is configured to add the mixed feed stream above the surface of the liquid ammonia, below the surface of the liquid ammonia, or a combination thereof. In other variations, the reactor is configured to agitate the liquid ammonia while the mixed feed stream is added. In yet other variations, the reactor is configured to agitate the mixed feed stream while the mixed feed stream is added to the liquid ammonia, in some variations, reactor 110 comprises an inert packed bed, in some variations, a gas-liquid reaction occurs through the inert packed bed, wherein atomized mixed feed stream and a counter current of ammonia flow through the inert packed bed. In some variations of the forgoing, the ammonia is in gaseous form. In other variations of the forgoing, the ammonia is in liquid form, in other variations, the system further comprises a controller configured to isothermally control the combining of the mixed feed stream with ammonia. As described above with respect to the integrated methods, by controlling the reaction conditions of this step, the reaction may be driven to selectively produce the compound of formula (2). With reference again to FIG. 3, hydroxypropanamide stream 114 is fed into reactor 120. Reactor 120 further receives dehydration agent 123. Hydroxypropanamide can then undergo dehydration in reactor 120 to produce amide products and/or nitrile products. In some variations, reactor 120 comprises a continuous packed bed vapor phase reactor. In yet other variations, reactor 120 comprises a multi-temperature stage column, in some variations, reactor 120 is operated at a temperature from about 380° C. to about 390° C., If should be understood that, in some variations as depicted in FIG. 3, hydroxypropanamide stream 114 does not require further processing to remove solvent and/or ammonia at this stage. Rather, solvent and/or ammonia may be carried through the integrated system and removed in distillation unit 122 as depicted in FIG. 3. Distillation unit 122 as depicted in FIG. 3 is connected to reactor 120. In some variations, distillation unit 122 may be a part of reactor 120. In other variations, distillation unit 122 may be a separate unit from reactor 120, and a product stream comprising amide products and/or nitrile products, solvent, ammonia and other components, is fed to distillation unit 122. Distillation unit 122 is configured to separate the products produced and components in reactor 120 into four separate streams 124-127 of a compound of formula (3-I) or isomers thereof, a compound of formula (3) or isomers thereof, solvent and ammonia. It should be understood, however, in other variations, the distillation unit may be configured to separate certain components from reactor 120. For example, in one variation, the distillation unit is focused on separating a compound of formula (3-I) and/or a compound of formula (3), or isomers thereof, without separating the solvent and/or ammonia that may be present in the system.

Thus, in certain aspects, provided is an integrated system, comprising: a first reactor configured to receive epoxide, carbon monoxide and solvent, and to produce a carbonylation product stream in the presence of carbonylation catalyst, wherein the carbonylation product stream comprises beta lactone, solvent and carbonylation catalyst; a separation unit configured to receive the carbonylation product stream, and to remove at least a portion of the carbonylation catalyst and form a mixed feed stream, wherein the mixed feed stream comprises beta lactone and solvent; a second reactor configured to receive the mixed feed stream and ammonia, and to produce a hydroxypropanamide stream, wherein the hydroxypropanamide stream comprises hydroxypropanamide, solvent and ammonia; and a third reactor configured to receive the hydroxypropanamide stream and dehydration agent, and to produce a product stream, wherein the product stream comprises amide and/or nitrile products, solvent and ammonia.

In some variations, the integrated system comprises: an epoxide source configured to output an epoxide stream; a carbon monoxide source configured to output a carbon monoxide stream; a solvent source configured to output a solvent stream; a first reactor comprising: at least one inlet configured to receive epoxide, carbon monoxide, and solvent, and an outlet to output a carbonylation product stream produced in the presence of carbonylation catalyst in the first reactor, wherein the carbonylation product stream comprises beta lactone, solvent and carbonylation catalyst; a separation unit configured to receive the carbonylation product stream, and to remove at least a portion of the carbonylation catalyst and form a mixed feed stream, wherein the mixed feed stream comprises beta lactone and solvent; an ammonia source configured to output ammonia; a second reactor comprising: at least one inlet configured to receive the mixed feed stream and ammonia, and an outlet configured to output a hydroxypropanamide stream, wherein the hydroxypropanamide stream comprises hydroxypropanamide, solvent and ammonia; and a third reactor comprising: an inlet configured to receive the hydroxypropanamide stream, and an outlet configured to produce a product stream in the presence of dehydration agent, wherein the product stream comprises amide and/or nitrile products, solvent and ammonia.

Although FIG. 3 depicts an exemplary system that includes separation unit 107 to remove carbonylation catalyst from the carbonylation product stream, in other variations where heterogeneous carbonylation catalyst is used, such separation unit may not be required. For example, in other aspects, the system comprises: a first reactor configured to receive epoxide, carbon monoxide and solvent, and to produce a mixed feed stream in the presence of carbonylation catalyst, wherein the mixed feed stream comprises beta lactone, solvent and carbonylation catalyst; a second reactor configured to receive the mixed feed stream and ammonia, and to produce a hydroxypropanamide stream, wherein the hydroxypropanamide stream comprises hydroxypropanamide, solvent and ammonia; and a third reactor configured to receive the hydroxypropanamide stream and dehydration agent, and to produce a product stream, wherein the product stream comprises amide and/or nitrile products, solvent and ammonia.

Figure 4:
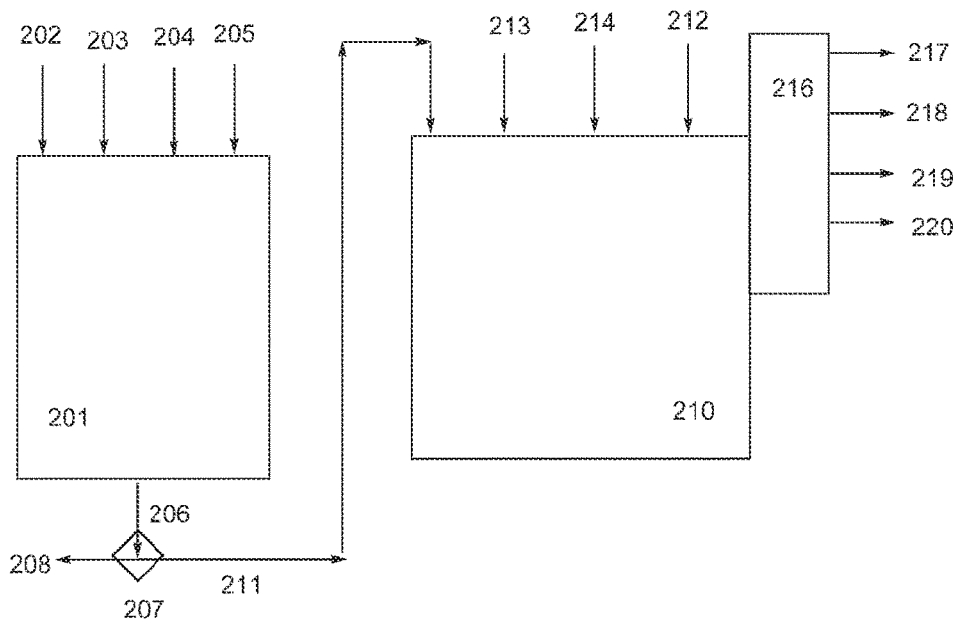

It should further be understood that although FIG. 3 depicts reactor 120 receiving dehydration agent 123, in other variations, dehydration agent 123 may be contained in reactor 120, for example, in a catalyst bed. Although FIG. 3 depicts an exemplary system to produce amide products and/or nitrile products from epoxide and carbon monoxide, it should be understood that in other variations, the beta lactone and/or hydroxypropanamide may be obtained from commercially available sources. Other variations of the exemplary system depicted in FIG. 3 are also contemplated. For example, the mixed feed stream may be combined with ammonia and dehydration agent in one reactor to produce the product stream. With reference to FIG. 4, system 200 is an exemplary system for the integrated production of amide products and/or nitrile products, in which the mixed feed stream is combined with ammonia and dehydration agent in one reactor to produce the product stream.

System 200 includes reactor 201, within which the carbonylation of epoxide takes place. Epoxide 202, carbon monoxide 203, solvent 204 and carbonylation catalyst 205 are fed into reactor 201. Epoxide is carbonylation in the presence of carbonylation catalyst and solvent to produce carbonylation product stream 206, which comprises the compound of formula (1), solvent and carbonylation catalyst. Carbonylation product stream 208 may undergo further processing steps to remove carbonylation catalyst. As depicted in FIG. 4, carbonylation product stream 208 is directed to a separation unit 207, which separates carbonylation catalyst 208 and yields mixed feed stream 211, which comprises the compound of formula (1) and solvent. Recovered carbonylation catalyst 208 may be reused and recycled back into system 200.

Without requiring further processing of mixed feed stream 211 to remove solvent, mixed feed stream 211 is fed into reactor 210. Reactor 210 also receives ammonia 212, dehydration agent 213, and optionally base 214. Hydroxypropanamide can then undergo dehydration in reactor 210 to produce amide products and/or nitrile products. Distillation unit 216, which may be integrated as part of reactor 210 or a separate unit from reactor 210, separates into four separate streams 217-220 of a compound of formula (3-I) or isomers thereof, a compound of formula (3) or isomers thereof, solvent and ammonia, it should be understood, however, in other variations, the distillation unit may be configured to separate certain components from reactor 210. For example, in one variation, the distillation unit is focused on separating a compound of formula (3-I) and/or a compound of formula (3), or isomers thereof, without separating the solvent and/or ammonia that may be present in the system.

In other variations, carrier gas may be used in the conversion of hydroxypropanamide to amide products and/or nitrile products. Thus, in certain aspects, provided is a system comprising a reactor configured to receive a hydroxypropanamide stream with carrier gas and dehydration agent, and to output a product stream comprising the compound of formula (3-I) and/or the compound of formula (3), or isomers thereof. In some variations, the carrier gas comprises ammonia. In other variations, the carrier gas comprises ammonia and nitrogen. In some variations, the product stream further comprises ammonia, water, or a combination thereof.

Figure 5:
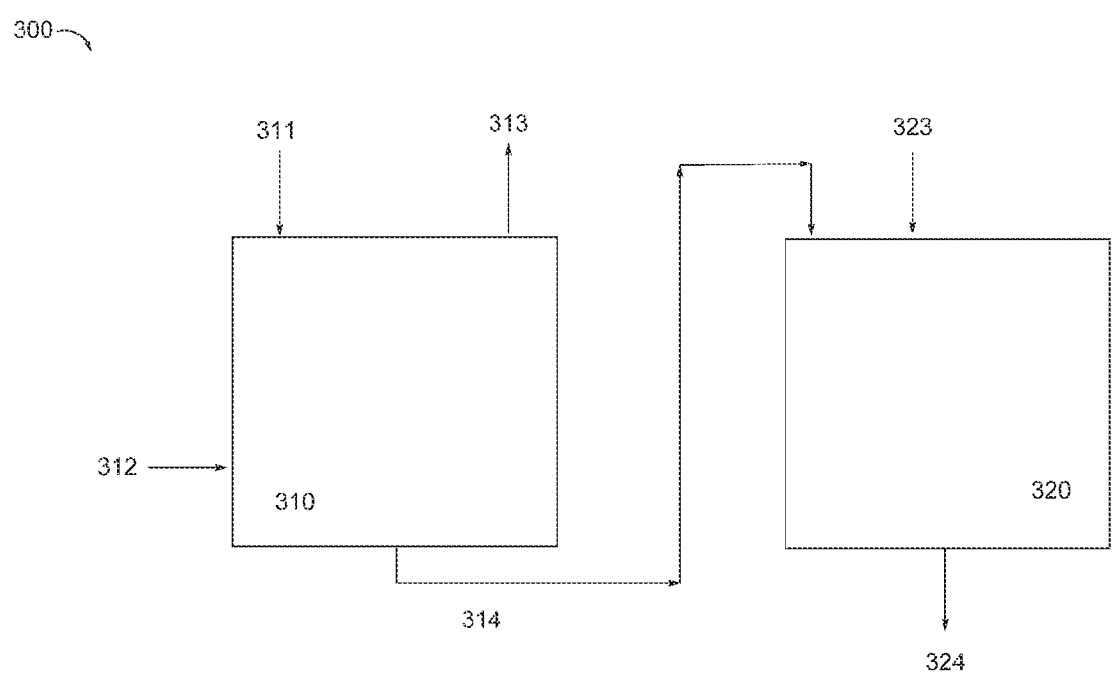

With reference to FIG. 5, system 300 is another exemplary system for the integrated production of amide products and/or nitrile products. System 399 includes reactor 310 and reactor 320. Reactor 310 receives mixed feed stream 311 and ammonia 312, and outputs stream 313, which may include excess ammonia, solvent and/or lights, and hydroxypropanamide stream 314. Reaction vessel 320 receives hydroxypropanamide stream 314 and carrier gas 323. Reaction vessel 320 contains dehydration agent (not depicted in FIG. 5). Reaction vessel 329 outputs product stream 324. In some variations, product stream 324 may be further treated to isolate a compound of formula (3-I) and/or a compound of formula (3), wherein the compound of formula (3-I) and/or a compound of formula (3) are as defined herein, ammonia, or water, or any combination thereof.

The reaction vessels described in the systems herein are configured to operate at any suitable temperatures and/or pressures. In some variations, the reaction vessels described in the systems herein are equipped to maintain the contents of said reaction vessels under a positive pressure of an inert gas. In some embodiments, the inert gas comprises nitrogen. The reaction vessels described in the systems herein are equipped to off gas gases. In some embodiments, the reaction vessels described in the systems herein are equipped to off gas ammonia. The reaction vessels described in the systems herein are equipped to remove volatiles, in some embodiments, the volatiles comprise ammonia and other gases. The reaction vessels described in the systems herein are equipped to transfer any of the streams described herein, in some variations, the reaction vessels are configured to receive streams from any other reaction vessels so described in the systems herein, in other variations, the reaction vessels are configured to output streams to any other reaction vessels so described in the systems herein, in some variations, the reaction vessels are configured to output streams to a downstream plant or to storage, or any combination thereof.

In some variations, any of the systems described herein can be configured to operate in a continuous process, in other variations, any of the reaction systems described herein can be configured to operate in a batch process. In other variations, any of the reaction systems described herein can be configured to operate in a semi-batch process. In other variations, any of the reaction systems described herein can be configured to operate in a semi-continuous process. In some variations, the reactors described in the systems herein can be any container suitable for containing the reagents and products involved in a reaction of interest. The reactors may be configured as a receptacle, tank, chamber, pressure vessel, well, or other structure capable of containing solids, liquids, and may be sealed to contain gaseous reaction mixtures. The reactors include one or more inlets to provide reagents and/or outlets to remove intermediates and/or products. The reactors can be a stand-alone unit or it can be one of an array of multiple units. The volume of the reactors may vary within the scope of the invention. The material of the reaction vessel may by any suitable material for containing reagents and products involved in a reaction of interest prior to, during, and after the reaction of interest. The reactors may include a means for providing heat to the reagents and products involved in a reaction of interest. Such means may include use of a heating jacket, heating coils, heating tubes, or heat exchangers, or any combination thereof. The reactors may include a means for providing mixing reagents and products involved in a reaction of interest. Such means may include use of a mechanical agitator. Examples of mechanical agitators include axial flow impellers and radial flow impellers.

The various aspects of the integrated methods and systems are explored in further detail below, including the carbonylation product stream, the mixed feed stream, the hydroxypropanamide stream, and the product stream. Also explored below are the acrylamide and acrylonitrile compounds and other compounds that may be produced using the integrated methods, as well as the amides, lactones, solvents, dehydration agents, and the various other components that may be utilized in their production, Carbonylation Product Stream The carbonylation product stream is the resulting product from carbonylation of epoxide in the presence of carbonylation catalyst and solvent. Any suitable methods and conditions may be employed for the carbonylation reaction. See e.g., WO 2013/083191 and WO 2016/130977. In some embodiments, the carbonylation catalyst comprises a metal porphyrin moiety coordinated with a metal carbonyl moiety. In some variations, the metal porphyrin moiety comprises an optionally substituted porphyrin. In other variations, the metal porphyrin moiety comprises an optionally substituted tetraphenylporphyrin. In other embodiments, the carbonylation catalyst comprises a metal salen moiety coordinated with a metal carbonyl moiety. In some variations, the metal salen moiety comprises an optionally substituted salen, in still other variations, the metal porphyrin moiety comprises aluminum or chromium. In still other variations, the metal porphyrin moiety comprises aluminum (III) or chromium (III). In yet other variations, the metal salen moiety comprises aluminum or chromium, in yet other variations, the metal salen moiety comprises aluminum (III) or chromium (III). In some embodiments, the metal carbonyl moiety comprises a monoanionic carbonyl complex of any metal from group 5, 7, or 9 of the periodic table, in other embodiments, the metal carbonyl moiety comprises a dianionic carbonyl complex of any metal from group 4 or 8 of the periodic table. It should be understood that in cases where the metal carbonyl moiety is dianionic, there will typically be two metal porphyrin or two metal salen moieties coordinated with each dianionic metal carbonyl moiety. In some variations, the metal carbonyl moiety comprises cobalt. In other variations, the metal carbonyl moiety comprises manganese. In still other variations, the metal carbonyl moiety comprises rhodium. In some embodiments, the metal carbonyl moiety comprises $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^-$, [Os $[Co(CO)_4]^-$, $[Cr_2(CO)_{10}]^{2-}$, $[Fe_2(CO)_8]^{2-}$, $[Tc(CO)_5]^-$, $[Re(CO)_5]^-$, or $[Mn(CO)_5]^-$ or any combination thereof, in other variations, the metal carbonyl moiety comprises $[Co(CO)_4]^-$.

In other variations of the foregoing, the carbonylation catalyst may be further coordinated with one or more solvents used in the systems and methods described herein, in one variation, the carbonylation catalyst further comprises THF. In certain variations, the THF is coordinated to the aluminum or chromium of the metal porphyrin moiety, in other variations, the THF is coordinated to the aluminum of the metal porphyrin moiety. In other variations, at least one THF is coordinated to the aluminum of the metal porphyrin moiety. In certain variations, the THF is coordinated to the aluminum or chromium of the metal salen moiety. In other variations, the THF is coordinated to the aluminum of the metal salen moiety, in other variations, at least one THF is coordinated to the aluminum of the metal salen moiety.

Any suitable carbonylation catalysts may also be used. See e.g., WO 2016/015019 and WO 2012/158573. The carbonylation catalysts may be homogenous or heterogeneous. In some embodiments when the carbonylation catalyst is homogenous, the resulting carbonylation product stream comprises carbonylation catalyst, in addition to the compound of formula (1) and the carbonylation reaction solvent used. The method may further require a separation step to remove at least a portion, or all, of the carbonylation catalyst in the carbonylation product stream, as depicted in FIG. 1. Any suitable methods or techniques to remove or isolate carbonylation catalyst from the carbonylation product stream may be employed. For example, a membrane, such as a nanofiltration membrane, may be used. Carbonylation catalyst may be recycled back to the carbonylation reactor for further use in the carbonylation reaction, in other embodiments when the carbonylation catalyst is heterogeneous (e.g., present in a fixed bed within the carbonylation reactor), the carbonylation catalyst may not be present in the resulting carbonylation product, and no additional separation step may be required to remove carbonylation catalyst. Any suitable carbonylation reaction solvents may be used. See e.g., WO 2016/130977. In some variations, the solvent comprises polar solvent. In other variations, the solvent comprises ether, in one variation, the solvent comprises tetrahydrofuran.

The integrated methods and systems described herein do not require the removal of solvent from the feed stream used to produce the hydroxypropanamide. In fact, that solvent may be carried throughout the integrated process, and may be removed from the final product stream containing the amide products and/or nitrile products (e.g., referring to produce stream 4 in the exemplary reaction schemes of FIGS. 1 and 2).

Mixed Feed Stream

The mixed feed stream, for example as depicted in FIG. 1, is obtained from processing the carbonylation stream to remove carbonylation catalyst. In some embodiments, the mixed feed stream comprises a beta lactone such as a compound of formula (1) and solvent. In some variations, the compound of formula (1) is:

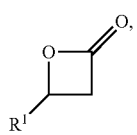

(1)

wherein $R^1$ is H, alkyl, alkenyl, cycloalkyl, or aryl. In some embodiments, wherein $R^1$ is H or alkyl.

It should be understood, however, that in embodiments of the integrated methods where heterogeneous carbonylation catalyst is used, the processing step described above to remove carbonylation catalyst may not be required. As noted above, the solvent may be carried throughout the integrated process, and may be removed from the final product stream containing the amide products and/or nitrile products (e.g., referring to produce stream 4 in the exemplary reaction schemes of FIGS. 1 and 2). With solvent present in the mixed feed stream, in some embodiments, the mixed feed stream is homogeneous. In other embodiments, the compound of formula (1) is at least partially soluble in the mixed feed stream. In other embodiments, the compound of formula (1) is soluble in the mixed feed stream, in some variations, the compound of formula (1) is soluble in the mixed feed stream at all operating temperatures described herein, Hydroxypropanamide Stream The hydroxypropanamide stream, for example as depicted in FIG. 1, may be obtained from reacting the mixed feed stream described herein with ammonia to produce hydroxypropanamide. The compound of formula (2) may be:

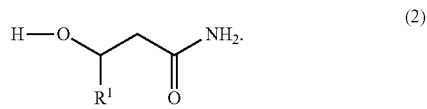

(2)

wherein $R^1$ is H, alkyl, alkenyl, cycloalkyl, or aryl. In some embodiments, wherein $R^1$ is H or alkyl.

Thus, in some embodiments, the hydroxypropanamide stream comprises a compound of formula (2), solvent and ammonia. The solvent and ammonia may be present in the hydroxypropanamide stream when such hydroxypropanamide stream is derived from the carbonylation of epoxide, as depicted in the exemplary reaction scheme of FIG. 1. In some embodiments, such solvent and ammonia may be carried throughout the integrated process and may be removed from the final product stream containing the amide products and/or nitrile products (e.g., referring to produce stream 4 in the exemplary reaction scheme of FIG. 1). In other variations of the integrated systems and method, the hydroxypropanamide stream may undergo further processing to remove at least a portion of the solvent and/or ammonia present therein.

In some embodiments, any of the hydroxypropanamide streams described herein further comprise additional products, such as a hydroxypropanamide such as the compound of formula (2-I) and/or an oligomer. In some variations, the compound of formula (2-I) is:

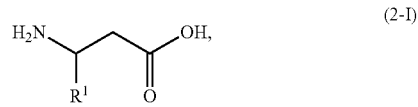

(2-I)

wherein $R^1$ is H, alkyl, alkenyl, cycloalkyl, or aryl. In some embodiments, wherein $R^1$ is H or alkyl. For example, in some variations, $R^1$ is H, and the compound of formula (2-I) is beta-alanine.

In some embodiments, the hydroxypropanamide stream has a molar ratio of the compound of formula (2) to additional products, of between 100:1 to about 1:1, between 100:1 to about 10:1, or between 100:1 to about 50:1; or about 100:1; about 50:1; or about 10:1. In some variations, the hydroxypropanamide stream comprises trace of additional products. In other variations, the hydroxypropanamide stream is substantially free of additional products. In one variation, "substantially free of additional products" refers to less than 1% (w/w), less than 5% (w/w), less than 10% (w/w), less than 15% (w/w) or less than 20% of additional products present in the stream. In other variations, "substantially free of additional products" refers to up to 20% (w/w) by weight of additional products present in the stream. In some variations, the hydroxypropanamide stream has a molar ratio of the compound of formula (2) to beta-alanine of between 100:1 to about 1:1, between 100:1 to about 10:1, or between 100:1 to about 50:1; or about 100:1; about 50:1; or about 10:1. In some embodiments, the hydroxypropanamide stream comprises trace beta-alanine. In other embodiments, the bydroxypropanamide stream is substantially free of beta-alanine. In one variation, "substantially free of beta-alanine" refers to less than 1% (w/w), less than 5% (w/w), less than 10% (w/w), less than 15% (w/w) or less than 20% of beta-alanine present in the stream. In some variations, the hydroxypropanamide stream has a molar ratio of the compound of formula (2) to oligomer of between 100:1 to about 1:1, between 100:1 to about 10:1, or between 100:1 to about 50:1; or about 100:1; about 50:1; or about 10:1. In some embodiments, the hydroxypropanamide stream comprises trace oligomer. In other embodiments, the hydroxypropanamide stream is substantially free of oligomer. In one variation, "substantially free of oligomer" refers to less than 1% (w/w), less than 5% (w/w), less than 10% (w/w), less than 15% (w/w) or less than 20% of oligomer present in the stream. In other variations, "substantially free of oligomer" refers to up to 20% (w/w) by weight of oligomer present in the stream.

In some embodiments, the hydroxypropanamide stream is treated to remove or isolate the additional products, such as the compound of formula (2-I) and/or oligomer from the hydroxypropanamide stream. In some embodiments, the hydroxypropanamide stream is homogeneous. In other embodiments, the compound of formula (2) is at least partially soluble in the hydroxypropanamide stream. In still other embodiments, the compound of formula (2) is soluble in the hydroxypropanamide stream, in some variations, the compound of formula (2) is soluble in the hydroxypropanamide stream at all operating temperatures described herein. As discussed above, since the hydroxypropanamide stream may obtained from the mixed feed stream described herein, any additional components present in the reaction to produce the mixed feed stream may be carried into the hydroxypropanamide stream. For example, in some embodiments of the integrated methods, the mixed feed stream and ammonia (including, for example, anhydrous ammonia) may be further combined with base to produce hydroxypropanamide. In such an embodiment, the hydroxypropanamide stream would further comprise base, in addition to the other components as described above. If base is present in the hydroxypropanamide stream, the integrated methods may further comprise an additional step of removing at least a portion of the base, prior to the dehydration reaction to produce the amide products and/or nitrile products.

In another variation, carrier gas may be added to the hydroxypropanamide stream, or carrier gas may be combined with the hydroxypropanamide stream in the reaction to produce the amide products and/or nitrile products. For example, in one aspect, provided is a method comprising: contacting a hydroxypropanamide stream with a heterogeneous dehydration agent to produce the product stream (as described herein), wherein the hydroxypropanamide stream comprises molten compound of formula (2) (as described herein) and carrier gas. In another aspect, provided is a method comprising: contacting a hydroxypropanamide stream and carrier gas with a heterogeneous dehydration agent to produce the product stream (as described herein), wherein the hydroxypropanamide stream comprises molten compound of formula (2). In some variations of the foregoing aspects, the hydroxypropanamide stream further comprises ammonia and/or vaporized solvent, in another variation, the hydroxypropanamide stream further comprises ammonia, and is further combined with vaporized solvent. It should be understood that, in certain embodiments of the integrated methods, a hydroxypropanamide stream may not be formed and/or isolated. For example, with reference again to FIG. 2, a hydroxypropanamide stream may not be formed and/or isolated if the mixed feed stream is reacted with ammonia and dehydration reaction together, or in one reaction vessel, to produce the amide products and/or nitrile products.

Product Stream

The product stream comprises the amide products and/or nitrile products produced from hydroxypropanamide. In some variations, the products are an unsaturated nitrile or unsaturated amide compound. The products may correspond to compound of formula (3-I) and/or a compound of formula (3):

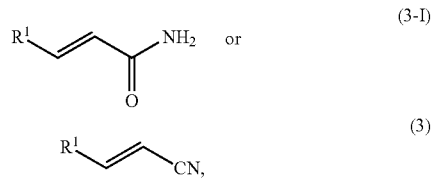

or isomers thereof, wherein $R^1$ is H, alkyl, alkenyl, cycloalkyl, or aryl. In some embodiments, wherein $R^1$ is H or alkyl. Thus, in some embodiments, the product stream comprises a compound of formula (3-I) or isomers thereof, a compound of formula (3) or isomers thereof, solvent and ammonia. The solvent and ammonia may be present in the product stream when such product stream is derived from the carbonylation of epoxide, as depicted in the exemplary reaction schemes of FIGS. 1 and 2. In some embodiments, such solvent and ammonia may be carried throughout the integrated process, and then removed from the product stream.

In some variations, the integrated methods further comprise separating one or more components of the product stream. Any suitable methods may be used to separate the components in the product stream. For example, in one variation, distillation may be used. For example, in one variation, the integrated methods further comprise isolating the compound of formula (3-I) and/or the compound of formula (3), or isomers thereof. Aside from isolating the amide products and/or nitrile products, one or more of the other components present in the product stream may also be isolated and recovered. For example, in certain variations, the method further comprises isolating the ammonia and/or solvent. Such recovered ammonia and/or solvent may be reused in any of the methods or systems described herein. As discussed above, since the product stream may obtained from the mixed feed stream described herein, any additional components present in the reaction to produce the mixed feed stream may be carried into the product stream. For example, in some embodiments of the integrated methods, the mixed feed stream and ammonia (including, for example, anhydrous ammonia) may be further combined with base to produce hydroxypropanamide. In such an embodiment, the hydroxypropanamide stream would further comprise base, in addition to the other components as described above. If the base that is present in the hydroxypropanamide stream is not removed prior to the dehydration reaction, then the product stream will also include base. Thu, in some variation if base in present in the product stream, the product stream may undergo further processing to isolate and recover the base. Such recovered base may be reused in any of the methods or systems described herein. Similarly, as discussed above, if carrier gas is present in the conversion of hydroxypropanamide to the amide products and/or nitrile products, then carrier gas may also be present in the product stream, if the carrier gas is present in the product stream, the product stream may undergo further processing to isolate and recover the carrier gas. Such recovered carrier gas may be reused in any of the methods or systems described herein.

Acrylonitrile Compounds and Other Nitrile Compounds

In some embodiments, the acrylonitrile compounds and other nitrile compounds produced according to the methods herein are compounds of formula (3):

(3)

or isomers thereof, wherein $R^1$ is H, alkyl, alkenyl, cycloalkyl, or aryl. "Alkyl" refers to a monoradical unbranched or branched saturated hydrocarbon chain. In some embodiments, alkyl has 1 to 10 carbon atoms (i.e., $C_{1-10}$ alkyl), 1 to 9 carbon atoms (i.e., $C_{1-9}$ alkyl), 1 to 8 carbon atoms (i.e., $C_{1-8}$ alkyl), 1 to 7 carbon atoms (i.e., $C_{1-7}$ alkyl), 1 to 6 carbon atoms (i.e., $C_{1-6}$ alkyl), 1 to 5 carbon atoms (i.e., $C_{1-5}$ alkyl), 1 to 4 carbon atoms (i.e., $C_{1-4}$ alkyl), 1 to 3 carbon atoms (i.e., $C_{1-3}$ alkyl), or 1 to 2 carbon atoms (i.e., $C_{1-2}$ alkyl). Examples of alkyl include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbon atoms is named, ail geometric isomers having that number of carbon atoms may be encompassed; thus, for example, "butyl" can include n-butyl, sec-butyl, isobutyl and t-butyl; "propyl" can include n-propyl and isopropyl. Further, it should be understood that when a range of values is listed, it is intended to encompass each value and sub-range within the range. For example, "$C_{1-6}$ alkyl" (which may also be referred to as $_{1-6}$ C alkyl, $C_1$-$C_6$ alkyl, or $C_{1-6}$ alkyl) is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl, "Alkenyl" refers to an unsaturated linear or branched monovalent hydrocarbon chain or combination thereof, having at least one site of olefinic unsaturation (i.e., having at least one moiety of the formula C=C). In some embodiments, alkenyl has 2 to 10 carbon atoms (i.e., $C_{2-10}$ alkenyl). The alkenyl group may be in "cis" or "trans" configurations, or alternatively in "E" or "Z" configurations. Examples of alkenyl include ethenyl, allyl, prop-1-enyl, prop-2-enyl, 2-methylprop-1-enyl, but-1-enyl, but-2-enyl, but-3-enyl, isomers thereof, and the like. "Cycloalkyl" refers to a carbocyclic non-aromatic group that is connected via a ring carbon atom. Examples of cycloalkyl include cyclopropyl, cyclobutyl, cyclopentyl, cyclohexyl, and the like. "Aryl" refers to a monovalent aromatic carbocyclic group of from 6 to 18 annular carbon atoms having a single ring or a ring system having multiple condensed rings. Examples of aryl include phenyl, naphthyl and the like. In some variations, the alkyl, alkenyl, cycloalkyl, or aryl for FT may be optionally substituted. The term "optionally substituted" means that the specified group is unsubstituted or substituted by one or more substituent groups. In certain variations, the optional substituents may include halo, —$OSO_2R_2$, —$OSiR_4$, —OR, C=$CR_2$, —R, —OC(O)R, —C(O)OR, and —C(O)$NR_2$, wherein R is independently H, optionally substituted alkyl, optionally substituted alkenyl, or optionally substituted aryl. In some embodiments, R is independently unsubstituted alkyl, unsubstituted alkenyl, or unsubstituted aryl. In some embodiments, R is independently H, methyl (Me), ethyl (Et), propyl (Pr), butyl (Bu), benzyl (Bn), allyl, phenyl (Ph), or a haloalkyl. In certain embodiments, substituents may include F, Cl, —$OSO_2Me$, —OTBS (where "TBS" is tert-butyl(dimethyl)silyl)), —OMOM (where "MOM" is methoxymethyl acetal), —OMe, —OEt, —O/Pr, —OPh, —$OCH_2CHCH_2$, —OBn, —$OCH_2$(furyl), —$OCF_2CHF_2$, —C=$CH_2$, —OC(O)Me, —OC(O)nPr, —OC(O)Ph, —OC(O)C(Me)$CH_2$, —C(O)OMe, —C(O)OnPr, —C(O)$NMe_2$, —CN, -Ph, —$C_6F_5$, —$C_6H_4OMe$, and —OH. In certain embodiments, $R^1$ is FI or alkyl, in some variations, $R^1$ is H, and the compound of formula (3) corresponds to the formula

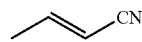

is (also known in the art as acrylonitrile). In other variations, $R^1$ is alkyl, in certain variations, $R^1$ is $C_{1-6}$ alkyl, in one variation, $R^1$ is methyl or ethyl. When $R^1$ is methyl, the compound of formula (3) is

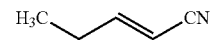

or isomers thereof (also known in the art as crotononitrile). When $R^1$ is ethyl, the compound of formula (3) is or isomers thereof (also known in the art as 2-pentenenitrile)

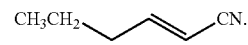

Acrylamides and Other Amides

In some embodiments, acrylamide or other amides may be used to produce the acrylonitrile compounds and other nitrile compounds. In some variations, such amides correspond to the formula (3-1)

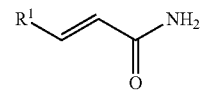

wherein $R^1$ is H, alkyl, alkenyl, cycloalkyl, or aryl, in certain embodiments. $R^1$ is H or alkyl.

In some variations, $R^1$ is H, and the compound corresponds to the formula (3-I), And is known as acrylamide

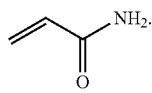

In other variations, $R^1$ is alkyl. In certain variations, $R^1$ is $C_{1-6}$ alkyl. In one variation, $R^1$ is methyl or ethyl. When $R^1$ is methyl, the compound of formula (3-I) is

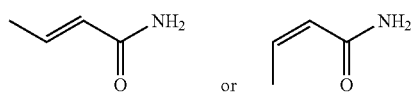

(also known in the art as but-2-enamide). When $R^1$ is ethyl, the compound of formula (2) is

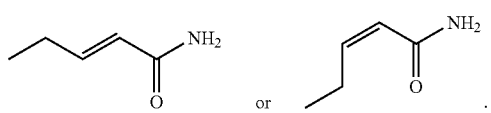

(also known in the art as pent-2-enamide). It should generally be understood that when a compound of formula (3-I), or isomers thereof, is used to produce a compound of formula (3), or isomers thereof, $R^1$ of formula (3-I) is as defined for formula (3). Acrylamides and other amides, such as the compounds of formula (3-I) may be obtained from the methods described herein, or any commercially available sources, or produced according to any methods known in the art. In certain aspects, the compounds of formula (3-I) produced according to the methods herein may be isolated. In some variations, the compounds of formula (3-I) produced according to the methods herein may be isolated and purified. The compounds of formula (3-1) produced according to the methods herein may be isolated, Beta-Hydroxy Amides and Other Hydroxy Amides In some embodiments, the beta-hydroxy amides and other hydroxy amides that may be used to produce the acrylonitrile compounds and other nitrile compounds according to the methods herein are compounds of formula (2):

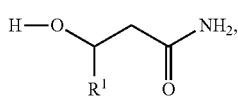

(2)

wherein $R^1$ is H, alkyl, alkenyl, cycloalkyl, or aryl. In certain embodiments, $R^1$ is H or alkyl. In some variations, $R^1$ is H, and the compound of formula (2) is

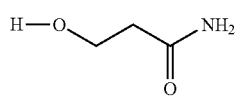

(or 3-hydroxypropanamide). In other variations, $R^1$ is alkyl. In certain variations, $R^1$ is $C_{1-6}$ alkyl. In one variation, $R^1$ is methyl or ethyl. When $R^1$ is methyl, the compound of formula (2) is

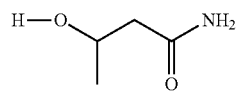

(or 3-hydroxybutanamide). When $R^1$ is ethyl, the compound of formula (2) is

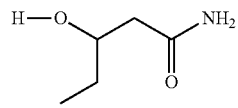

or 3-hydroxypentanamide).

It should generally be understood that when a compound of formula (2) is used to produce a compound of formula (3), or isomers thereof, $R^1$ of formula (2) is as defined for formula (3). The beta-hydroxy amides and other amides, such as the compounds of formula (2) may be obtained from the methods described herein, or any commercially available sources, or produced according to any methods known in the art. In certain aspects, the compounds of formula (2) produced according to the methods herein may be isolated. In some variations, the compounds of formula (2) produced according to the methods herein may be isolated and purified. The compounds of formula (2) produced according to the methods herein may be isolated.

Beta-Lactones and Other Lactones

In some embodiments, the beta-lactones may be used to produce beta-hydroxy amides, acrylamide, acrylonitrile and other compounds according to the methods herein. In certain embodiments, the beta-lactones are compounds of formula (1):

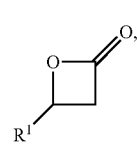

(1)

wherein $R^1$ is H, alkyl, alkenyl, cycloalkyl, or aryl, in certain embodiments, $R^1$ is H or alkyl, in some variations, $R^1$ is H, and the compound of formula (1) is

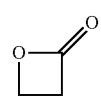

in the art (also known as beta-propiolactone). In other variations, $R^1$ is alkyl. In certain variations, $R^1$ is $C_{1-6}$ alkyl. In one variation, $R^1$ is methyl or ethyl. When $R^1$ is methyl, the compound of formula (1) is

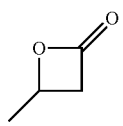

also known in the art as beta-butyrolactone). When $R^1$ is ethyl, the compound of formula (1) is

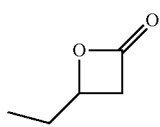

(also known in the art as beta-valerolactone).

The beta-lactones, such as the compounds of formula (1), may be obtained from any commercially available sources or produced according to any methods known in the art. For example, beta-propiolactone may be obtained by reacting ethylene oxide and carbon monoxide under suitable conditions. In some variations, the amide products and/or nitrile products may be produced from any of the beta-lactones provided in Column B of Table A below. As shown in Table A, such beta-lactones in Column B may be produced from the corresponding epoxide from Column A of the table.

TABLE A

| Column A | Column B |
|---|---|
| (epoxide) | (β-propiolactone) |
| (propylene oxide) | (β-butyrolactone) or/and (β-butyrolactone isomer) |
| (epichlorohydrin, Cl) | (β-lactone, Cl) |
| (epoxide, CF₃) | (β-lactone, CF₃) |
| (glycidyl mesylate, O-SO₂Me) | (β-lactone, O-SO₂Me) |
| (glycidyl OTBS) | (β-lactone, OTBS) |
| (glycidyl OMe) | (β-lactone, OMe) |
| (glycidyl OEt) | (β-lactone, OEt) |

TABLE A-continued
| Column A | Column B |
|---|---|
| 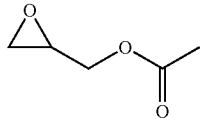 | 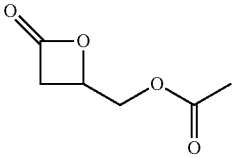 |
| 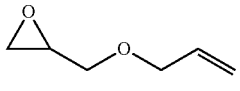 | 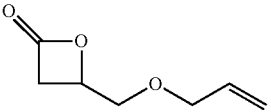 |
| 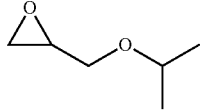 | 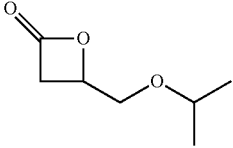 |
| 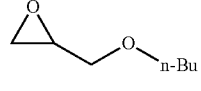 | 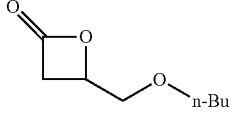 |
| 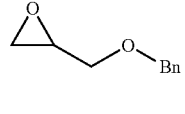 | 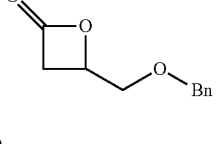 |
| 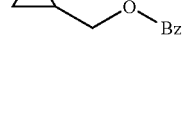 | 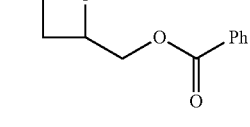 |
| 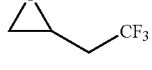 | 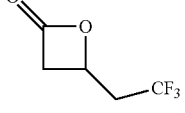 |
| 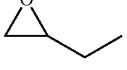 | 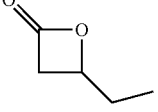 |
| 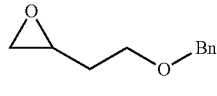 | 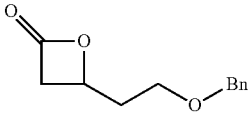 [SMILES: O=C1CC(CCOCc2ccccc2)O1] |
| 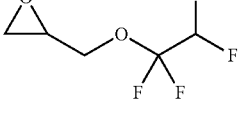 | 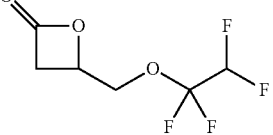 |

TABLE A-continued
| Column A | Column B |
|---|---|
| 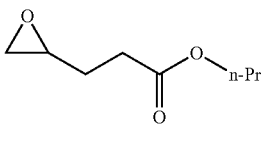 | 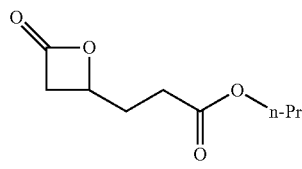 |
| 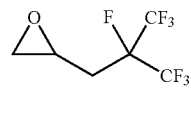 | 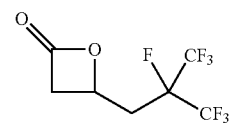 |
| 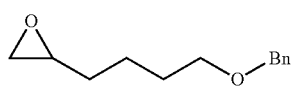 [SMILES: c1ccc(COCCCCC2CO2)cc1] | 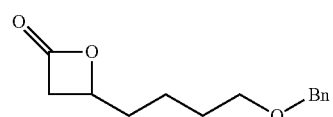 |
| 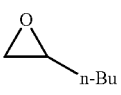 | 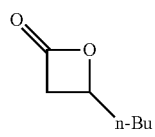 |
| 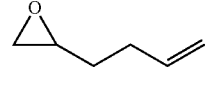 | 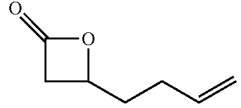 |
| 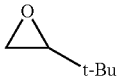 | 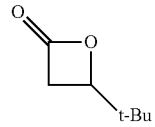 |
| 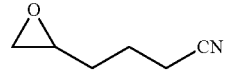 |  |
| 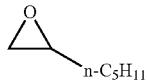 | 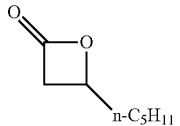 |
| 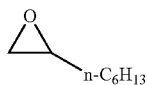 | 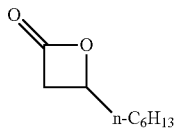 |
| 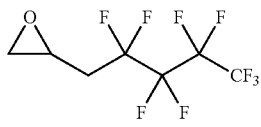 [SMILES: FC(F)(F)C(F)(F)C(F)(F)C(F)(F)CC1CO1] | 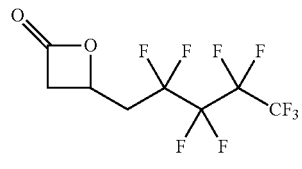 [SMILES: O=C1CC(CC(F)(F)C(F)(F)C(F)(F)C(F)(F)F)O1] |
| 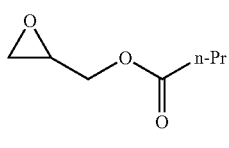 | 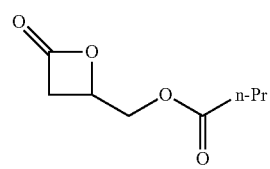 |

TABLE A-continued
| Column A | Column B |
|---|---|
| 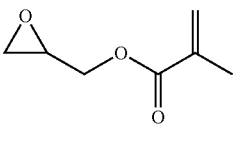 | 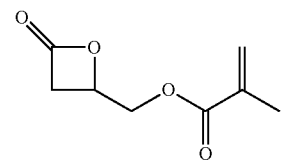 |
| 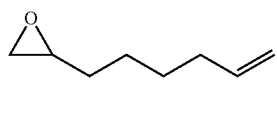 | 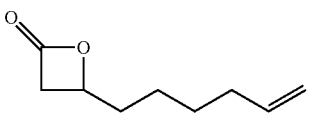 |
| 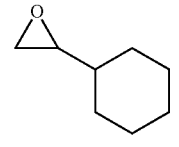 | 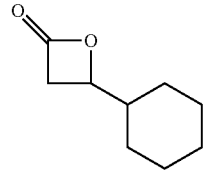 [SMILES: O=C1CC(C2CCCCC2)O1] |
| 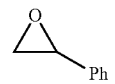 | 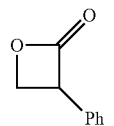 |
| 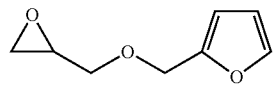 [SMILES: c1coc(COCC2CO2)c1] | 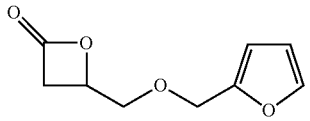 [SMILES: O=C1CC(COCc2ccco2)O1] |
| 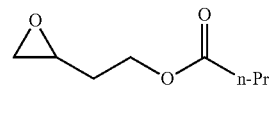 | 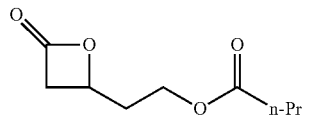 |
| 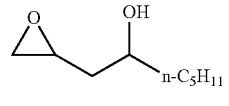 | 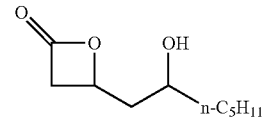 |
| 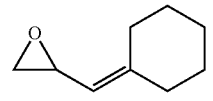 | 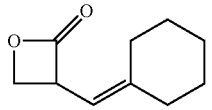 [SMILES: O=C1OCC1C=C1CCCCC1] |
| 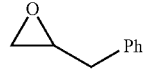 | 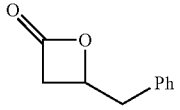 |
| 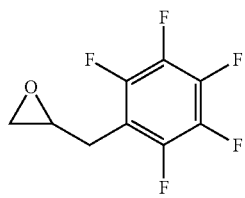 [SMILES: Fc1c(F)c(F)c(CC2CO2)c(F)c1F] | 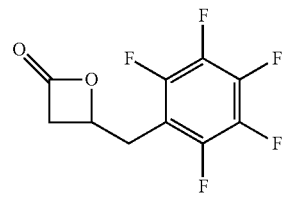 [SMILES: O=C1CC(Cc2c(F)c(F)c(F)c(F)c2F)O1] |
| 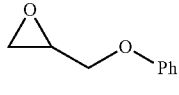 | 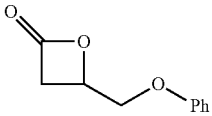 [SMILES: O=C1CC(COc2ccccc2)O1] |

TABLE A-continued
| Column A | Column B |
|---|---|
| 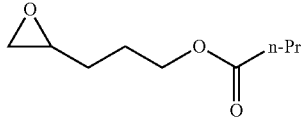 | 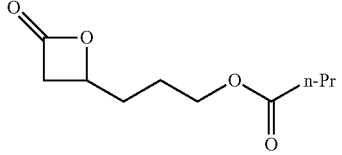 |
| 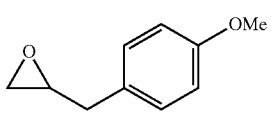 [SMILES: COc1ccc(CC2CO2)cc1] | 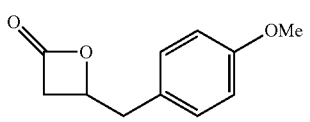 [SMILES: COc1ccc(CC2CC(=O)O2)cc1] |
| 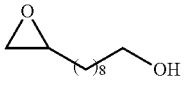 | 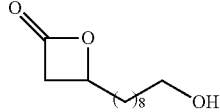 |
| 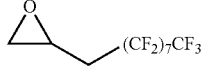 | 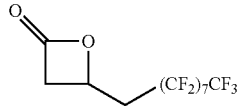 |
| 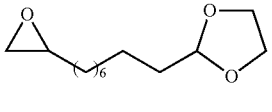 | 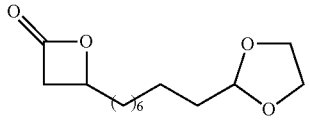 |
| 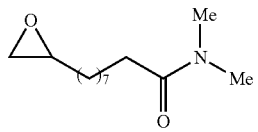 | 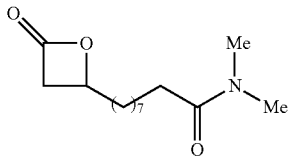 |
| 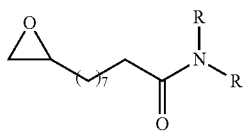 | 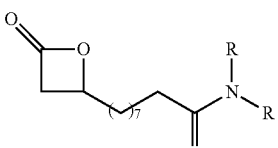 |
| 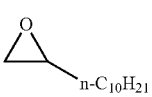 | 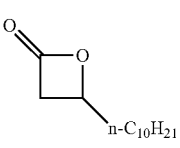 |
|  | 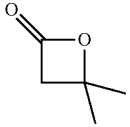
and/or
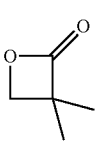 |

TABLE A-continued
| Column A | Column B |
|---|---|
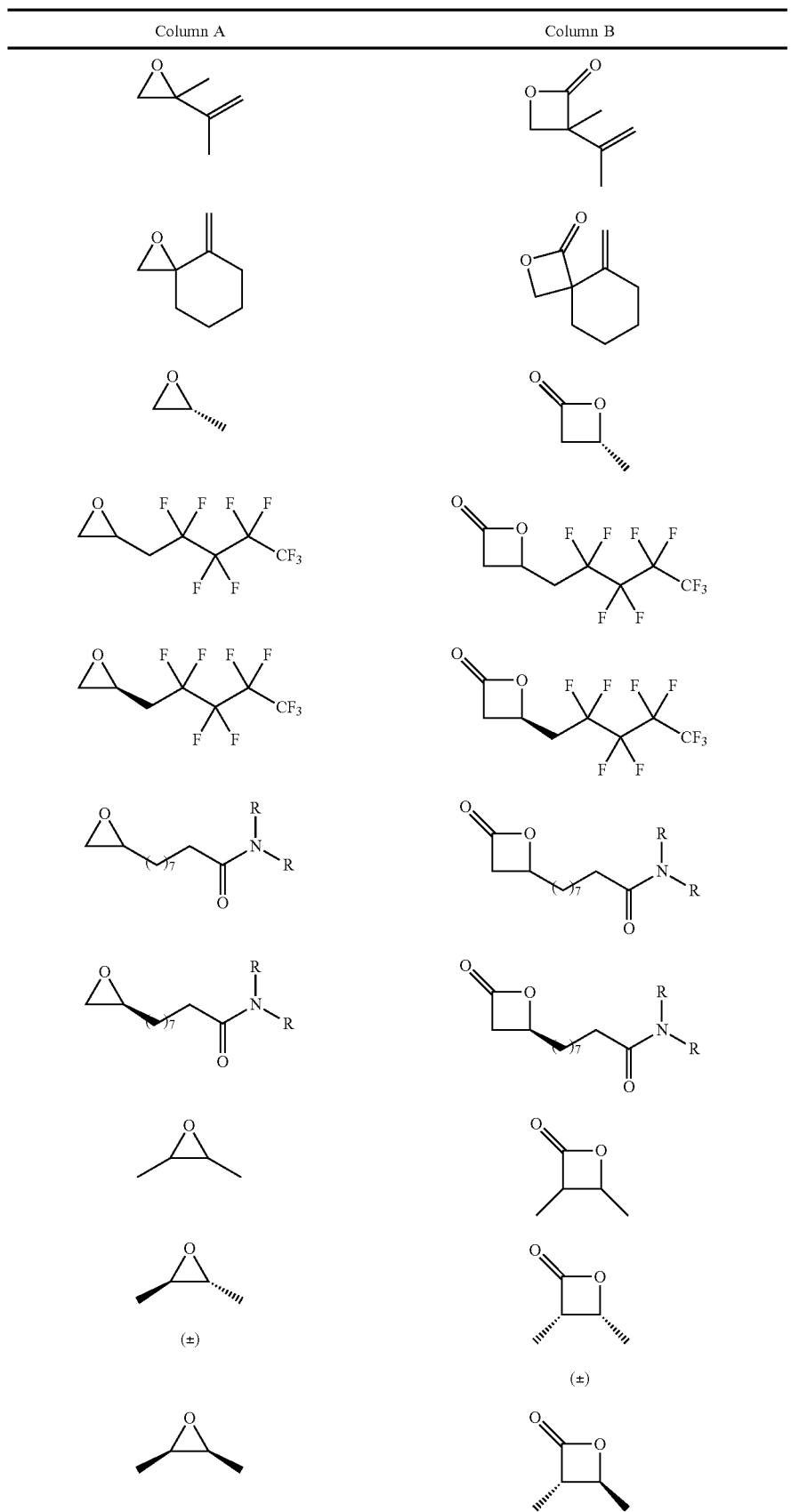

TABLE A-continued
| Column A | Column B |
|---|---|
| 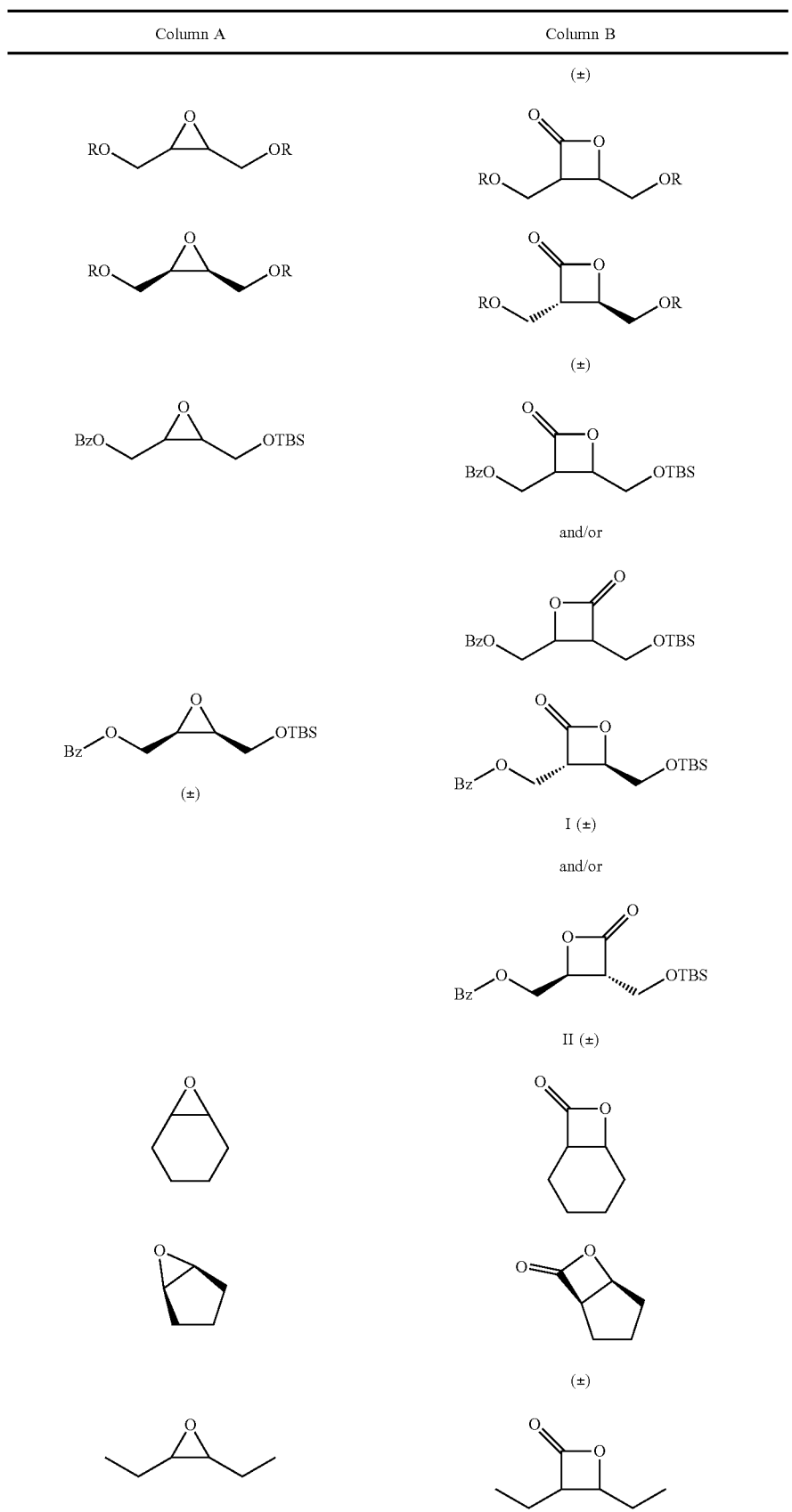 | |

TABLE A-continued
| Column A | Column B |
|---|---|
| 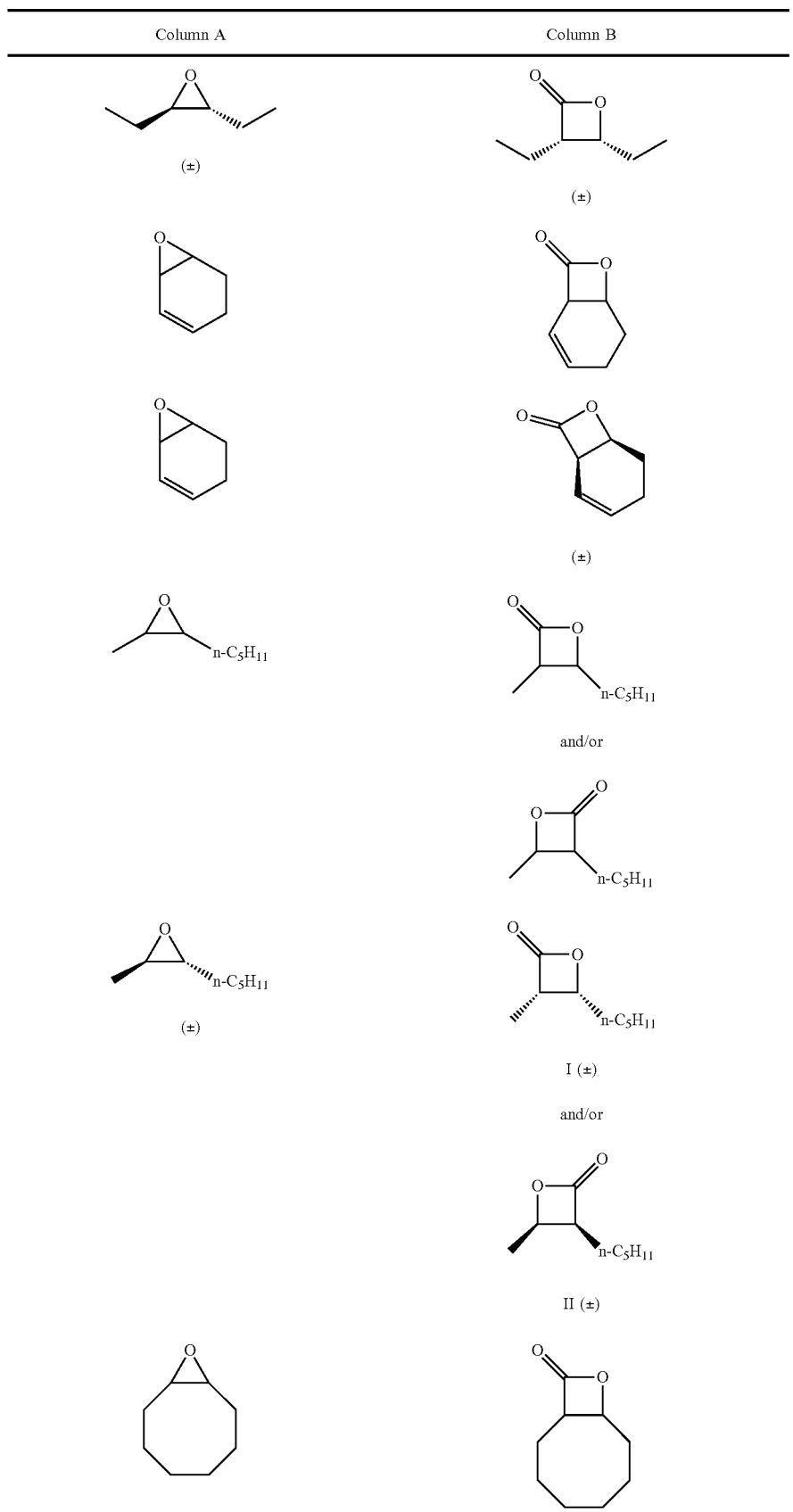 | |

TABLE A-continued
| Column A | Column B |
|---|---|
| 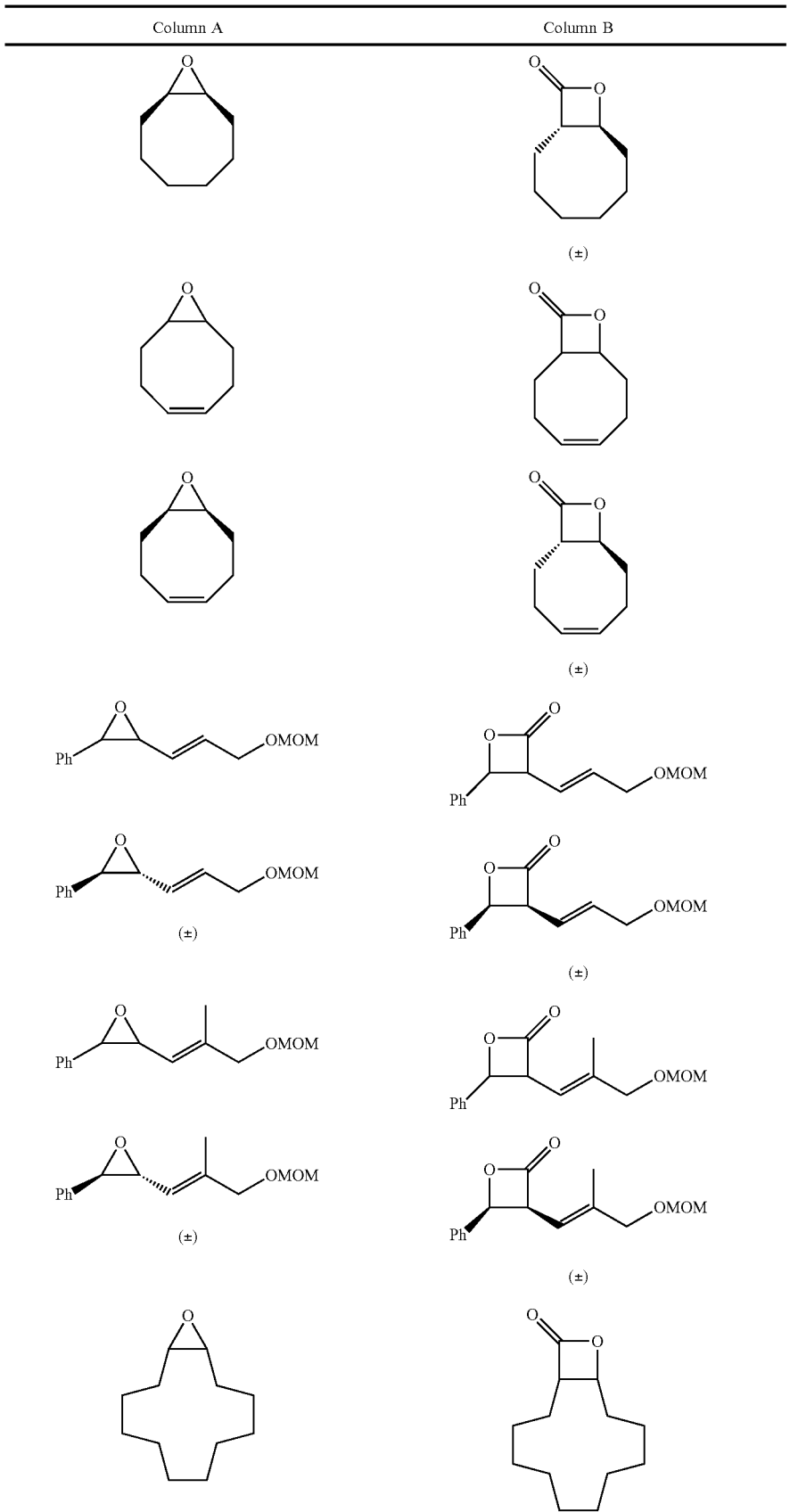 | |

TABLE A-continued
| Column A | Column B |
|---|---|
| 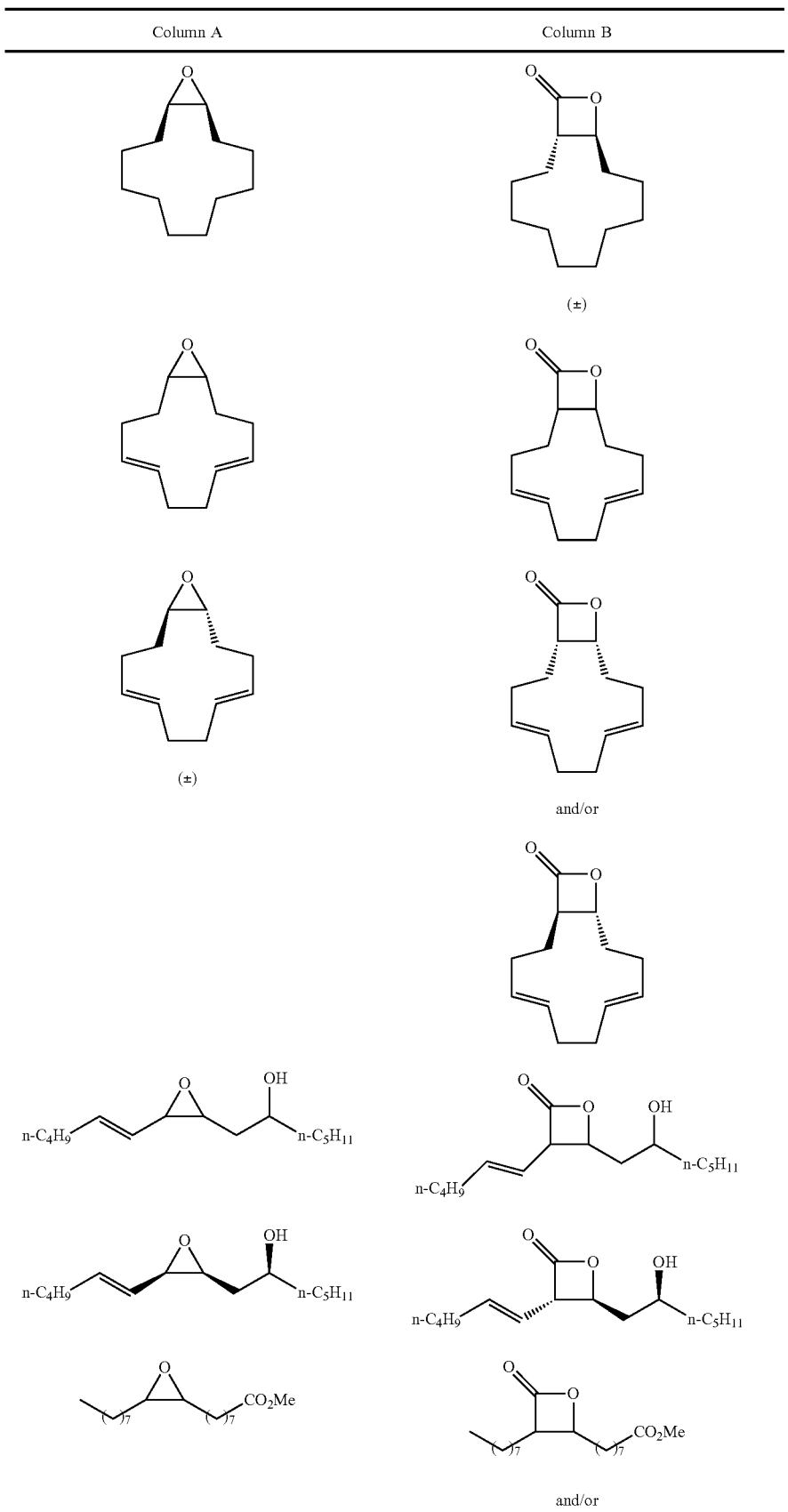 | |

TABLE A-continued

| Column A | Column B |
|---|---|

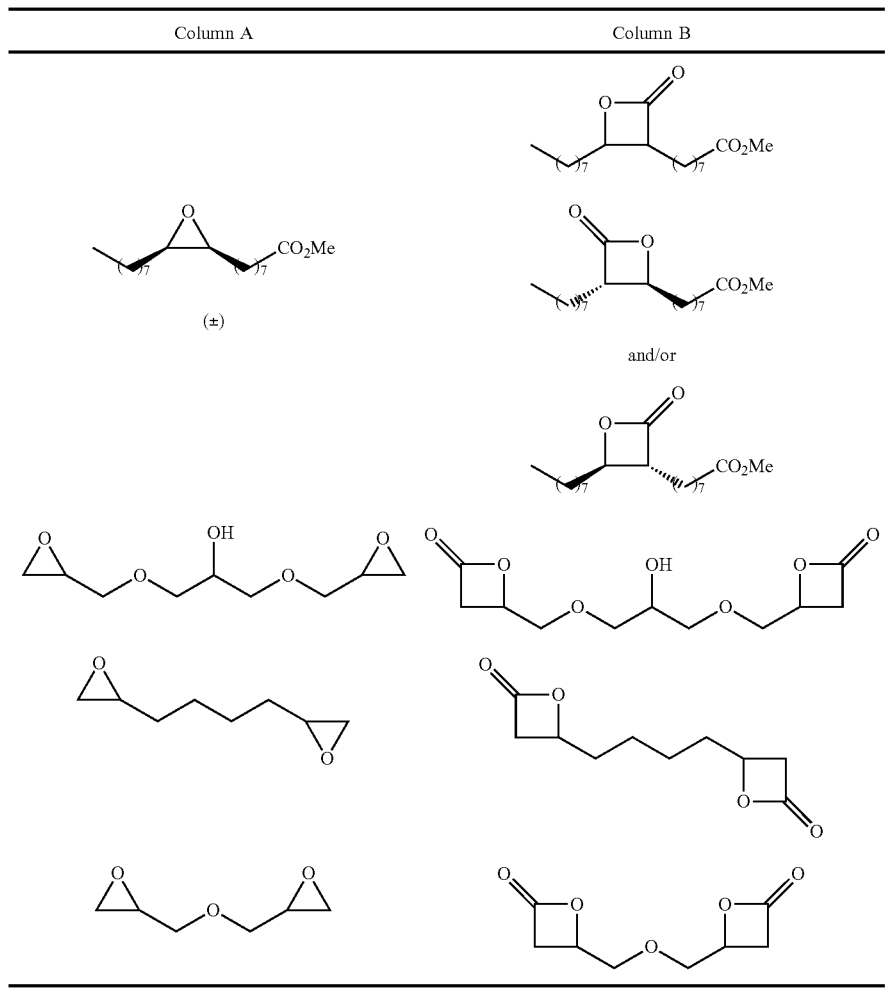

The beta-lactones, such as the compounds of formula (1), may be obtained from renewable feedstock. For example, when beta-propiolactone is produced from ethylene oxide and carbon monoxide, either or both the ethylene oxide and carbon monoxide may be obtained from renewable feedstock using methods known in the art. When the beta-lactone, such as the compound of formula (1), is obtained in part or completely from renewable feedstock, the polyamide produced according to the methods described herein from such beta-lactone has a biocontent greater than 0%. Various techniques are known in the art to determine biocontent of a material. For example, in some variations, biocontent of a material may be measured using the ASTM D6866 method, which allows the determination of the biocontent of materials using radiocarbon analysis by accelerator mass spectrometry, liquid scintillation counting, and isotope mass spectrometry. A biocontent result may be derived by assigning 100% equal to 107.5 pMC (percent modern carbon) and 0% equal to 0 pMC. For example, a sample measuring 99 pMC will give an equivalent biocontent result of 93%. In one variation, biocontent may be determined in accordance with ASTM D6866 revision 12 (i.e., ASTM D6866-12). In another variation, biocontent may be determined in accordance with the procedures of Method B of ASTM-D6866-12. Other techniques for assessing the biocontent of materials are described in U.S. Pat. Nos. 3,885,155, 4,427,884, 4,973,841, 5,438,194, and 5,881,299, as well as WO2009/155086.

Ammonia

The ammonia described herein may be obtained from any commercially available sources, or produced according to any methods known in the art. In some embodiments, the ammonia comprises anhydrous ammonia, in other embodiments, the ammonia comprises liquid ammonia. In still other embodiments, the ammonia comprises liquid anhydrous ammonia. In some variations, the ammonia is anhydrous ammonia. In other variations, the ammonia is liquid ammonia. In yet other variations, the ammonia is liquid anhydrous ammonia, in some variations of the foregoing, the ammonia may further comprise wafer, in such variations, the ammonia comprises at least 0.1%, at least 1%, at least 5%, at least 10%, at least 15%, or at least 30% by weight of water, in other variations, the ammonia comprises at least 40%, at least 50%, at least 60%, at least 70%, at least 80%, or at least 90% by weight of water. In still other variations, the ammonia comprises between about 0.1 wt % to about 15 wt % water, 0.1 wt % to about 10 wt % water, or 0.1 wt % to about 1 wt % water. In some embodiments, the ammonia is the carrier gas in any of the systems and methods described herein. In other embodiments, the ammonia is a component of the carrier gas in any of the systems and methods described herein. In such instances, the other components of the carrier gas may include nitrogen, vaporized solvent, or a combination thereof, in some embodiments, the ammonia is present in excess in any of the methods or systems described herein. In some embodiments, the ammonia is volatile. In other embodiments, the ammonia is volatile and is removed from any of the systems or methods described herein by distillation. In some variations, the distillation comprises vacuum distillation. In other variations, the ammonia is removed from any of the systems or methods described herein by vacuum. In still other variations, the ammonia is removed from any of the systems or methods described herein by off-gassing the ammonia, in some variations, the ammonia is removed from the hydroxypropanamide stream. In some variations, the ammonia is removed from the hydroxypropanamide stream by off-gassing the ammonia from the hydroxypropanamide stream, in other variations, the ammonia is removed from the product stream, in other variations, the ammonia is removed from the product stream by off-gassing the ammonia from the product stream, in yet other embodiments, at least a portion of the ammonia is allowed to off-gas, but some of the ammonia stays with the hydroxypropanamide stream to solubilize the compound of formula (2). In some variations, the compound of formula (2) is 3-hydroxypropanamide (3-HPA). In such variations, allowing the 3-HPA dissolved in ammonia to partially off-gas may provide a semi-viscous liquid that may be used as a replacement for molten 3-HPA. In any of the foregoing embodiments, the removed ammonia may be recovered to storage and/or reused in any of the methods or systems described herein.

Solvent

Figure 2:
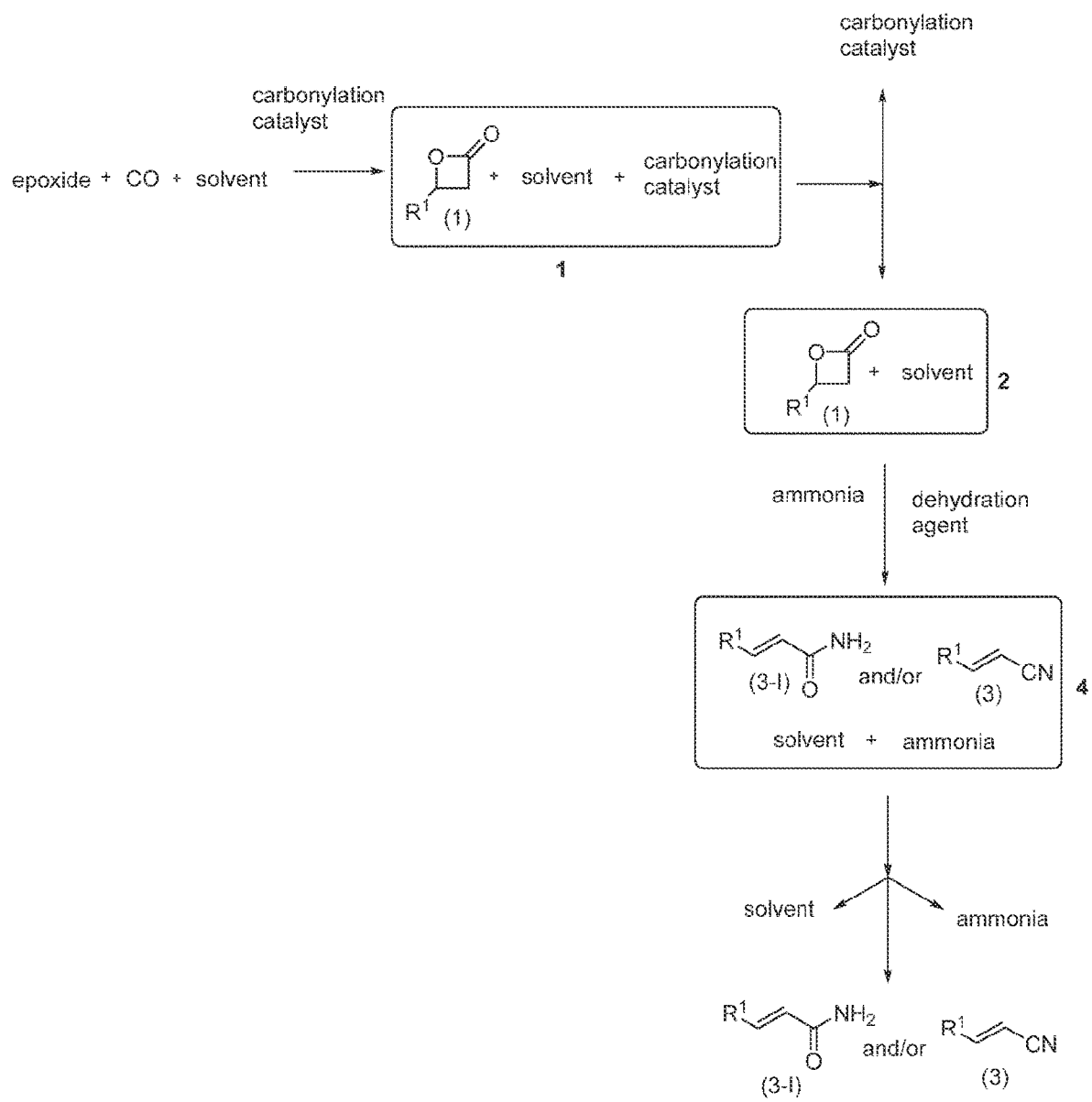

The solvents described herein may be obtained from any commercially available sources, or produced according to any methods known in the art. With reference to FIGS. 1 and 2, it should be understood that the solvent present throughout the integrated methods may be carbonylation solvent, used in the first step of the exemplary reactions in FIGS. 1 and 2 to produce the carbonylation product stream. Thus, in some variations, the solvent may also be referred to as carbonylation solvent. In some embodiments, the solvent comprises polar solvent. In other embodiments, the solvent comprises polar aprotic solvent. In some variations, the solvent comprises ether, in other variations, the solvent comprises tetrahydrofuran. In some embodiments, the solvent comprises a polar protic solvent. In some variations, the solvent comprises an alcoholic solvent. In other variations, the solvent comprises an alcohol, in still other variations, the alcohol comprises a $C_1$-$C_{10}$ alcohol, in some embodiments, the alcohol comprises ethanol. In some embodiments, the solvent comprise ethanol. In some embodiments, the solvent comprises a polar aprotic solvent and an alcohol. In some variations, the solvent comprises ether and alcohol. In one variation, the ether is tetrahydrofuran, in another variation, the alcohol is ethanol. In some embodiments, the solvent is used as a carrier gas in any of the systems and methods described herein. In other embodiments, the solvent is used as a component of the carrier gas in any of the systems and methods described herein, in the foregoing embodiments, the solvent is vaporized. In such instances, the other components of the carrier gas may include nitrogen, ammonia, or a combination thereof. In some embodiments, the solvent is removed from any of the systems or methods described herein by distillation. In some variations, the distillation comprises vacuum distillation, in other variations, the solvent is removed from any of the systems or methods described herein by vacuum. In some variations, the solvent is removed from the hydroxypropanamide stream. In other variations, the solvent is removed from the product stream. In any of the foregoing embodiments, the removed solvent may be recovered to storage and/or reused in any of the methods or systems described herein.

Carrier Gas

The carrier gas described herein may be obtained from any commercially available sources, or produced according to any methods known in the art. In some embodiments, the carrier gas described herein facilitates passage of any of the beta-hydroxy amides described herein through any of the dehydration agents described herein. In other variations, the carrier gas described herein facilitates passage of any of the hydroxypropanamide streams described herein through any of the dehydration agents described herein. In still other variations, the carrier gas described herein facilitates passage of any of the mixed feed streams described herein through any of the dehydration agents described herein. In some variations of the foregoing, the dehydration agent is heterogeneous. In some variations of the foregoing, the dehydration agent is a heterogeneous dehydration agent. In other variations, any of the beta-hydroxy amides, hydroxypropanamide streams, or mixed feed streams described herein are mixed/vaporized with carrier gas and continuously fed to a fixed bed reactor which is packed with dehydration agent, in still other variations, any of the beta-hydroxy amides, hydroxypropanamide streams, or mixed feed streams described herein are vaporized in the absence of additional carrier gas and continuously fed to a fixed bed reactor which is packed with dehydration agent, in such instances, various components of the beta-hydroxy amides, hydroxypropanamide streams, or mixed teed streams may comprise the carrier gas. For example, in the case of a hydroxypropanamide stream comprising compound of formula (2), solvent, and ammonia, the vaporized solvent and/or ammonia may comprise the carrier gas. In some embodiments, the carrier gas comprises nitrogen. In other embodiments, the carrier gas comprises ammonia, in some variations, the carrier gas comprises nitrogen and ammonia. In other variations, the carrier gas comprises nitrogen, ammonia, and vaporized solvent. In still other variations, the carrier gas comprises nitrogen and vaporized solvent. In yet other variations, the carrier gas comprises ammonia and vaporized solvent. In some variations, the carrier gas comprises nitrogen and ammonia, wherein the relative volume of ammonia gas ranges from about 1% to about 99%, about 30% to about 99%, about 60% to about 99%, about 90% to about 99%, about 1% to about 60%, about 1% to about 30%, or about 1% to about 10% with respect to the nitrogen gas.

Base

The bases described herein may be obtained from any commercially available sources, or produced according to any methods known in the art. In some embodiments, the bases described herein facilitate the ring opening of any of the beta-lactones described herein. In some embodiments, the bases described herein facilitate the conversion of any of the beta-lactones described herein to produce any of the beta-hydroxy amides, acrylamides, acrylonitriles and other compounds described herein, according to any of the methods or systems described herein. In some embodiments, the base comprises an amine. In some variations, the base comprises an aliphatic amine, in other variations, the base comprises an aromatic amine. The base may be a tertiary amine, a secondary amine, or a primary amine. In some variations, the base comprises triethylamine. In other variations, the base comprises trimethylamine. In some variations, the base comprises pyridine. In some embodiments, the base comprises a metal amide, a metal oxide, a mixed metal oxide, or a metal hydroxide, or any combination thereof. In some embodiments, the base comprises a metal amide, in some variations, the base comprises sodium amide, in other embodiments, the base comprises a metal oxide. In some variations, the base comprises calcium oxide, in still other embodiments, the base comprises a metal hydroxide. In some variations, the base comprises tetramethylammonium hydroxide. In still other embodiments, the base is heterogeneous. In some variations, the base comprises zeolites or day minerals, or a combination thereof. In some embodiments, the base is volatile, in other embodiments, the base is volatile and is removed from any of the systems or methods described herein by distillation. In some variations, the distillation comprises vacuum distillation, in other variations, the base is removed from any of the systems or methods described herein by vacuum. In some variations, the base is removed from the hydroxypropanamide stream, in other variations, the base is removed from the product stream. In any of the foregoing embodiments, the removed base may be recovered to storage and/or reused in any of the methods or systems described herein.

Dehydration Agents

Dehydration generally involves converting a carbon-carbon single bond to a carbon-carbon double bond, and produces a water molecule. The dehydration reactions described herein may take place in the presence of a suitable homogeneous or heterogeneous catalyst, in some embodiments, suitable dehydration catalysts may include acids, bases and oxides. Examples of suitable acids may include $H_2SO_4$, HCl, titanic acids, metal oxide hydrates, metal sulfates ($MSO_4$, where M may be Zn, Sn, Ca, Ba, Ni, Co, or other transition metals), metal oxide sulfates, metal phosphates (e.g., $M_3(PO_4)_2$, where M may be Ca, Ba), metal phosphates, metal oxide phosphates, carbon (e. g., transition metals on a carbon support), mineral acids, carboxylic acids, salts thereof, acidic resins, acidic zeolites, clays, $SiO_2/H_3PO_4$, fluorinated $Al_2O_3$, phosphotungstic acids, phosphomolybdic acids, silicomolybdic acids, silico tungstic acids and carbon dioxide. Examples of suitable bases may include NaOH, ammonia, polyvinylpyridine, metal hydroxides, $Zr(OH)_4$, and substituted amines. Examples of suitable oxides may include $Nb_2O_5$, $TiO_2$, $ZrO_2$, $Al_2O_3$, $SiO_2$, $ZnO_2$, $SnO_2$, $WO_3$, $MnO_2$, $Fe_2O_3$, and $V_2O_5$. In some embodiments, the dehydration agents used in the methods described herein include phosphorous pentoxide, an organophosphorous compound, a carbodiimide compound, a triazine compound, an organosilicon compound, a mixed oxide, a transition metal complex, or an aluminum complex. In certain embodiments, the dehydration agents used in the methods described herein may further comprise a solid support. Suitable solid supports may include, for example, hydrotalcite. The dehydration agents may be obtained from any commercially available sources or prepared according to any methods known in the art.

Phosphorous Compounds

The dehydration agent used in the methods described herein may comprise phosphorous compounds. In one variation, the dehydration agent comprises phosphorous pentoxide. In some variations, the dehydration agent comprises an organophosphorous compound, in certain variations, the organophosphorous compound is an organophosphate. In certain variations, the organophosphorous compound is an alkyl halophosphate or a cycloalkyl halophosphate, in one variation, the alkyl halophosphate is alkyl dihalophosphate or dialkyl halophosphate, in another variation, the cycloalkyl halophosphate is cycloalkyl dihalophosphate, or dicycloalkyl halophosphate. In some variations of the foregoing organophosphorous compounds, the alkyl is a $C_1$-$C_{10}$ alkyl, in other variations of the foregoing organophosphorous compounds, the cycloalkyl is a $C_3$-$C_{10}$ cycloalkyl, in some variations, cycloalkyl contains only C and H when unsubstituted. In other variations, cycloalkyl can have one ring or multiple rings, in other variations, cycloalkyl with more than one ring may be linked together by a C—C bond, fused, spiro or bridged, or combinations thereof, in some embodiments, cycloalkyl is a $C_3$-$C_{10}$ cycloalkyl. In yet other variations of the foregoing organophosphorous compounds, the halophosphate is chlorophosphate. In yet other variations of the foregoing organophosphorous compounds, the halophosphate is fluorophosphate. Suitable organophosphorous compounds used in the methods described herein may include, for example, ethyl dichlorophosphate, diethyl chlorophosphate, methyl dichlorophosphate, dimethyl chlorophosphate, ethyl difluorophosphate, diethyl fluorophosphate, methyl difluorophosphate, or dimethyl fluorophosphate, or any combination thereof.

Carbodiimide Compounds

In certain embodiments, the dehydration agent comprises a carbodiimide. The carbodiimide compound may correspond to the formula $R^4$—N=C=N-$R^5$, wherein each $R^4$ and $R^5$ is independently alkyl or cycloalkyl. In certain variations of the foregoing, $R^4$ and $R^5$ are different. In other variations of the foregoing, $R^4$ and $R^5$ are the same, in other variations, each $R^4$ and $R^5$ is independently cycloalkyl. In certain variations, each $R^4$ and $R^5$ is independently alkyl. In certain variations, each $R^4$ and $R^5$ is independently is independently $C_{1-6}$ alkyl, in one variation, each $R^4$ and $R^5$ is independently is methyl, ethyl or propyl. In another variation, $R^4$ and $R^5$ are both methyl, ethyl or propyl. In another variation, $R^4$ and $R^5$ are both cyclohexyl, in yet other variations, $R^4$ is alkyl, and $R^5$ is cycloalkyl.

Suitable carbodiimide compounds used in the methods described herein may include, for example,

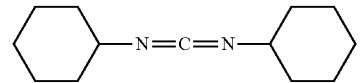

(also known in the art as N,N'-dicyclohexylcarbodiimide), in which $R^4$ and $R^5$ are both cyclohexyl.

Triazine Compounds

In certain embodiments, the dehydration agent comprises a triazine compound. In one variation, the triazine compound is 1, 3, 5-triazine, which has the following structure:

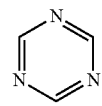

The triazine compounds described herein may be optionally substituted with one or more substituents. In some variations, the triazine compound is substituted with 1, 2 or 3 substituents, in certain variations, the substituents may be halo groups. For example, in certain variations, the triazine compound is a halo-substituted triazine compound. In certain variations, the triazine compound is 1, 3, 5-triazine substituted with 1, 2, or 3 halo groups. In one variation, the triazine compound is a halo-substituted 1, 3, 5-triazine. Exemplary triazine compounds used in the methods described herein may include, for example

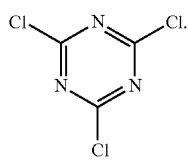

Cyanuric Chloride

Organosilicon Compounds

In certain embodiments, the dehydration agent comprises an organosilicon compound, in some variations, the organosilicon compound is a silazane. The silazane may be unsubstituted or substituted.

In one variation, the silazane is substituted with aryl, halo, alkyl, alkoxy or amino groups.

In certain embodiments, the organosilicon compound is,

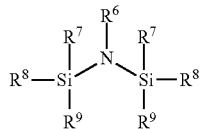

wherein each $R^6$, $R^7$, $R^8$ and $R^9$ (at each occurrence) is independently H, alkyl, cycloalkyl, heteroalkyl, heterocycloalkyl, aryl, heteroaryl, halo, amino, or alkoxy, in other variations, the organosilicon compound is a silane. The silane may be unsubstituted (e.g., a hydrosilane) or substituted. In some variations, the silane is substituted with 1, 2, 3 or 4 Substituents. In one variation, the silane is substituted with aryl, halo, alkyl, alkoxy or amino groups.

In certain embodiments, the organosilicon compound is

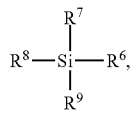

wherein each $R^6$, $R^7$, $R^8$ and $R^9$ is independently H, alkyl, cycloalkyl, heteroalkyl, heterocycloalkyl, aryl, heteroaryl, halo, amino, or alkoxy. In one embodiment, the organosilicon compound is an arylsilane. In some variations, the arylsilane comprises 1, 2 or 3 aryl groups. The variations of the foregoing, the aryl group is phenyl. Suitable arylsilanes may include, for example, diphenylsilane and phenylsilane. In one variation, the organosilicon compound is $Ph_2SiH_2$. In another variation, the organosilicon compound is $PhSiH_3$. In other embodiments, the organosilicon compound is a halosilane, an alkoxysilane, or an aminosilane. In one embodiment, the organosilicon compound is a halosilane. In some variations, the halosilane comprises 1, 2 or 3 halo groups. In certain variations, the halosilane may be further substituted with one or more substituents (other than halo). In one variation, the halosilane is further substituted with 1, 2 or 3 substituents (other than halo). In variations of the foregoing, the substituents of the halosilane are independently alkyl or aryl. In one variation of the foregoing, the alkyl substituent of the halosilane is $C_{1-6}$ alkyl. In another variation, the substituents of the halosilane are independently methyl or phenyl. Suitable halosilanes may include, for example, dialkyldihalosilane, aryltrihalosilane, arylalkyldihalosilane, or aryltrihalosilane, in certain variations, the halosilane is a chlorosilane. Suitable chlorosilanes may include, for example, dimethyldichlorosilane, phenyltrichlorosilane, or phenylmethyldichlorosilane. In another embodiment, the organosilicon compound is an alkoxysilane. In certain variations, the alkoxysilane comprises an alkylsilicate. In one variation, the alkoxysilane comprises a $C_{1-6}$ alkylsilicate. Suitable alkylsilicates include, for example, n-butylsilicate, in other variations, the alkoxysilane comprises 1, 2 or 3 alkoxy groups. In certain variations of the foregoing, the alkoxysilane may be further substituted with 1, 2 or 3 substituents (other than alkoxy). In one variation, the substituents of the alkoxysilane are independently alkyl or aryl. In one variation of the foregoing, the alkyl substituent of the alkoxysilane is $C_{1-6}$ alkyl. In another variation, the substituents of the alkoxysilane are independently methyl or phenyl. Suitable alkoxysilanes may include, for example, dimethoxy(methyl)phenylsilane. In yet another embodiment, the organosilicon compound is an aminosilane. In certain variations, the aminosilane is an alkylaminosilane. In certain variations of the foregoing, the aminosilane may be further substituted with 1, 2 or 3 substituents (other than an amino group, including, for example, an alkylamino group). In one variation, the substituents of the aminosilane are alkoxy groups, in one variation of the foregoing, the alkoxy substituent of the aminosilane is $C_{1-6}$ alkoxy. In another variation, the substituents of the aminosilane are independently methoxy or ethoxy. Suitable aminosilanes may include, for example, (3-aminopropyl)triethoxysilane. In other embodiments, the organosilicon compound is bis(trialkylsilyl)amine In one variation, the organosilicon compound is bis(trimethylsilyl)amine. In some variations of the foregoing, the silanes described herein may be used in combination with an alkylammonium halide as the dehydration agent, in one variation, the alkylammonium halide is tetrabutylammonium halide, such as tetrabutylammonium chloride or tetrabutylammonium fluoride. In certain variations, the organosilicon compound and the alkylammonium halide are provided as a mixture (e.g., in a solvent) or separately combined.

Transition Metal Complexes

In certain embodiments, the dehydration agent comprises a transition metal complex. In some variations, the transition metal complex comprises at least one halide or oxide ligand. The halide or oxide ligand may be associated or complexed with the transition metal. In certain variations of the foregoing, the transition metal complex is provided in a solvent. In other variations, the transition metal complex is provided in water or acetonitrile, or a mixture thereof. In one embodiment, the transition metal complex is a metal halide. In some variations, the metal halide comprises a Group 10 metal or a Group 12 metal. In certain variations, the metal halide comprises palladium or zinc. In certain variations, the metal halide comprises chloro. Suitable metal halides may include, for example, palladium chloride or zinc chloride. In some variations of the foregoing, the metal halide is provided in a solvent. In one variation, the metal halide is provided in water, acetonitrile or a mixture thereof. For example, the transition metal complex used in the methods described herein may be palladium chloride or zinc chloride provided in water, acetonitrile or a mixture thereof, in another embodiment, the transition metal complex comprises a Group 5 metal, in some variations, the transition metal complex comprises a vanadium oxide, in one variation, the vanadium oxide is monomeric vanadium oxide, in a certain variation, the dehydration agent comprises vanadium oxide and hydrotalcite. In one variation, the dehydration agent comprises monomeric vanadium oxide and hydrotalcite. The vanadium oxide (including, for example, monomeric vanadium oxide) may be incorporated on the surface of hydrotalcite.

Aluminum Complexes

In certain embodiments, the dehydration agent comprises an aluminum complex. In some variations, the aluminum complex comprises an aluminum halide. In certain variations, the aluminum complex is complexed with water, acetonitrile, or an alkali metal salt, or a mixture thereof. In some variations, the alkali metal salt is a sodium salt or a potassium salt. In some variations, the alkali metal salt is an alkali metal halide salt. In some variations, the alkali metal halide salt is an alkali metal iodide salt, in some variations, the alkali metal halide salt is sodium iodide or potassium iodide, in some variations, the aluminum complex is $AlCl_3.H_2O/KI/H_2O/CH_3CN$. In some variations, the aluminum complex is $AlCl_3.NaI$.

Other Heterogeneous Dehydrating Agents

In some variations, the dehydrating agents are heterogeneous. For example, in certain variations, the dehydration agent comprises a solid metal oxide, a solid acid, an acid, a weak acid, a strong acid, an ion-exchange resin, an aluminosilicate, or any combination thereof. In certain variations, the dehydration agent comprises a solid metal oxide, in one variation, the dehydration agent comprises $TiO_2$, $ZrO_2$, $Al_2O_3$, $SiO_2$, $ZnO_2$, $SnO_2$, $WO_3$, $MnO_2$, $Fe_2O_3$, $SiO_2/Al_2O_3$, $ZrO_2/WO_3$, $ZrO_2/Fe_2O_3$, or $ZrO_2/MnO_2$, or any combination thereof. In certain variations, the dehydration agent comprises a titanic acid, a metal oxide hydrate, a metal sulfate, a metal oxide sulfate, a metal phosphate, a metal oxide phosphate, a mineral acid, a carboxylic acid or a salt thereof, an acidic resin, an acidic zeolite, clay, or any combination thereof. In certain variations, the dehydration agent comprises $H_3PO_4/SiO_2$, fluorinated $Al_2O_3$, $Nb_2O_3/PO_4^{-3}$, $Nb_2O_5$, $H_3PO_4$, a phosphate salt, a phosphotungstic acid, a phosphomolybdic acid, a silicomolybdic acid, a silicotungstic acid, $Mg_2P_2O_7$ or $MgHPO_4$, or any combination thereof. In some variations, the dehydration agent comprises a zeolite. In certain variations, the zeolite is in hydrogen form or ammonia form, or is a metal-exchanged zeolite, in one variation, the metal-exchange zeolite comprises Li, Na, K, Ca, Mg, or Cu. In another variations, the zeolite has a pore size ranging from 1 to 10 angstroms in diameter, in one variation, the zeolite is a medium pore zeolite. In some variations, the zeolite has a pore size of about 5 to 6 angstroms, or about 5.6*6.0 angstroms, or about 5.1*5.5 to 5.3*5.6 angstroms. In another variation, the zeolite is a large pore zeolite. Suitable zeolites may include, for example, ZSM-12, ZSM-5, mordenite, faujasite, or zeolite Y. In variations where a heterogeneous dehydration agent, like the ones described above, are used, the compound of formula (2) undergoes dehydration to produce the compound of formula (3-I) or the compound of formula (3), or a combination thereof, by passing the compound of formula (2) in the vapor phase through a heated reactor containing the dehydration agent. In one variation, reactor is a packed bed reactor, a fluidized bed reactor, or a moving bed reactor, Combinations of Dehydration Agents It should be understood that, in some variations, the term "dehydration agent" may include a combination of agents. In some variations of the methods described herein, a combination of the dehydration agents described herein may be used, in some embodiments, the dehydration agent comprises a combination of an organosilicon compound and a transition metal complex. In certain variations of the foregoing combination, the organosilicon compound is N-methyl-N-(trimethylsilyl)trifluoroacetamide. In some variations of the foregoing combination, the transition metal complex is a metal triflate or a metal halide, in one variation, the metal triflate is zinc triflate. In another variation, the metal halide is copper chloride. In other embodiments, the dehydration agent comprises a combination of a silane and a transition metal complex, in certain variations of the foregoing combination, the transition metal complex is an iron complex. In one variation, the dehydration agent comprises a combination of a silane and an iron complex, in other variations of the combination of a silane and a transition metal complex, the transition metal complex is metal carbonate, in certain variations, the metal carbonate comprises iron, in certain variations, the metal carbonate is an iron carbonate. Suitable metal carbonates include, for example, $Fe_2(CO)_9$. In some variations of the foregoing combination, the organosilicon compound is an alkoxyalkylsilane. In certain variations, the alkoxyalkylsilane is diethoxymethylsilane. In one variation, the dehydration agent comprises a combination of iron carbonate and an alkoxyalkylsilane. Exemplary combinations of dehydration agents that may be used in the methods described herein include zinc triflate and N-methyl-N-(trimethylsilyl)trifluoroacetamide; copper chloride and N-methyl-N-(trimethylsilyl)trifluoroacetamide; an iron complex and a silane; and iron carbonate and diethoxymethylsilane.

Certain Dehydration Agents

In certain variations, the dehydration agent comprises $TiO_2$ and/or $SiO_2$. These variations of the dehydration agent are explored in further detail below, it should be understood that the $TiO_2$ described herein may be provided in any suitable mineral form, including rutile or anatase forms. In certain variations, the use of $TiO_2$ as a dehydration agent in any of the methods and systems described herein unexpectedly resulted in formation of a compound of formula (3), to the total or at least partial exclusion of a compound of formula (3-I). For example, in some embodiments, a hydroxypropanamide stream comprising a compound of formula (2), solvent and ammonia, is combined with $TiO_2$ to produce a product stream comprising a compound of formula (3), or isomers thereof, solvent, and ammonia, in some variations of the foregoing, the hydroxypropanamide stream is combined with $TiO_2$ at a temperature of about 300° C. to about 450° C. In other variations, the hydroxypropanamide stream is combined with $TiO_2$ at a temperature of 350° C. to about 400° C. In still other variations, the hydroxypropanamide stream is combined with $TiO_2$ at a temperature of about 400° C. In yet other variations, the hydroxypropanamide stream is combined with $TiO_2$ at a temperature of 350° C. to 400° C. In some variations of the foregoing, the compound of formula (3) is acrylonitrile, and the compound of formula (2) is 3-hydroxypropanamide. the solvent may comprises tetrahydrofuran. In still other variations of the foregoing, the solvent comprises ethanol. In still other variations of the foregoing, the solvent comprises tetrahydrofuran and ethanol. In some variations of the foregoing, the product stream further comprises compound of formula (3-I). In some variations, the product stream comprises trace amounts of the compound of formula (3-I).

In certain variations, the use of $SiO_2$ as a dehydration agent in any of the methods and systems described herein unexpectedly resulted in formation of a compound of formula (3-I), to the total or at least partial exclusion of a compound of formula (3). For example, in some embodiments, a hydroxypropanamide stream comprising a compound of formula (2), solvent and ammonia, is combined with $SiO_2$ to produce a product stream comprising a compound of formula (3-I), or isomers thereof, solvent, and ammonia. In some variations of the foregoing, the hydroxypropanamide stream is combined with $SiO_2$ at a temperature of about 250° C. to about 350° C. In other variations, the hydroxypropanamide stream is combined with $SiO_2$ at a temperature of 250° C. to about 300° C., In still other variations, the hydroxypropanamide stream is combined with $SiO_2$ at a temperature of about 300° C., In yet other variations, the hydroxypropanamide stream is combined with $SiO_2$ at a temperature of 300° C. In some variations of the foregoing, the compound of formula (3-I) is acrylamide, and the compound of formula (2) is 3-hydroxypropanamide. In still other variations of the foregoing, the solvent comprises tetrahydrofuran. In still other variations of the foregoing, the solvent comprises ethanol, in still other variations of the foregoing, the solvent comprises tetrahydrofuran and ethanol. In some variations of the foregoing, the product stream further comprises compound of formula (3). In some variations, the product stream comprises trace amounts of the compound of formula (3).

In some embodiments, the dehydration agent comprises $TiO_2$ and $SiO_2$. It was unexpectedly discovered that use of a combination of $TiO_2$ and $SiO_2$ as dehydration agent in any of the methods and systems described herein results in formation of a compound of formula (3), to the total or at least partial exclusion of a compound of formula (3-I). For example, in some embodiments, a hydroxypropanamide stream comprising a compound of formula (2), solvent and ammonia, is combined with a dehydration agent comprising $TiO_2$ and $SiO_2$ to produce a product stream comprising a compound of formula (3), or isomers thereof, solvent, and ammonia. In some variations of the foregoing, the hydroxypropanamide stream is combined with $TiO_2$ and $SiO_2$ at a temperature of about 250° C. to about 450° C. In some variations of the foregoing, the hydroxypropanamide stream is combined with $TiO_2$ and $SiO_2$ in a column, wherein the column has a zone comprising the $TiO_2$, and separately, a zone comprising the $SiO_2$. In some variations, the hydroxypropanamide stream is first passed through the zone comprising $SiO_2$, and is then passed through the zone comprising $TiO_2$. In other variations, the hydroxypropanamide stream is first passed through the zone comprising $TiO_2$, and is then passed through the zone comprising $SiO_2$. In some variations, the column is a multi-temperature stage column, in some variations, the zone comprising the $TiO_2$ operates at a first temperature, and the zone comprising the $SiO_2$ operates at a second temperature, wherein the first temperature and second temperature are different, in some variations, the first temperature is higher than the second temperature, in other variations, the first temperature is 390° C. to 400° C., and the second temperature is about 250° C. to 300° C. In some variations of the foregoing, the compound of formula (3) is acrylonitrile, and the compound of formula (2) is 3-hydroxypropanamide. In other variations of the foregoing, the solvent comprises tetrahydrofuran. In still other variations of the foregoing, the solvent comprises ethanol. In still other variations of the foregoing, the solvent comprises tetrahydrofuran and ethanol. In still other variations of the foregoing, the solvent is absent. In such variations, the compound of formula (2) may be dissolved in ammonia, in some variations of the foregoing, the product stream further comprises compound of formula (3-I). In some variations, the product stream comprises trace amounts of the compound of formula (3-I).

Lights

The various streams in the integrated methods and systems described herein, including the carbonylation product stream, the mixed feed stream, the hydroxypropanamide stream and/or the product stream may further comprise lights, in some variations, lights are low boiling components from any upstream process that are not isolated by distillation. In some variations, the lights comprise solvent or reactants from any upstream process, in other variations, the lights comprise ethylene oxide, acetaldehyde, or carbon monoxide, or any combination thereof. The lights from a given stream may be removed at any point in the process or may be carried through the process and removed in the final product stream. Thus, in some variations of the integrated methods and systems described herein, at least a portion of the lights may be removed, and a given stream may have less than 10%, less than 5%, less than 1%, or less than 0.1% by weight of lights. For example, in one variation, the mixed feed stream has less than 10%, less than 5%, less than 1%, or less than 0.1% by weight of lights.

Downstream Uses

The acrylamide, acrylonitrile and other compounds produced according to the integrated methods described herein and produced using the integrated systems described herein may, in some variations, be used as a monomer for the industrial production of polymers. The compounds of formulae (3-I) produced may be used to produce one or more downstream products. For example, acrylamide produced according to the methods described herein may be used in the production of polyacrylamide. Thus, in certain aspects, provided is a method, comprising: producing a compound of formula (3-I) according to any of the methods herein; and polymerizing the compound of formula (3-I). In one variation, provided is a method of producing polyacrylamide, comprising: producing acrylamide according to any of the methods herein; and polymerizing the acrylamide to produce polyacrylamide.

The compounds of formula (3) produced may be used to produce one or more downstream products. For example, acrylonitrile produced according to the methods described herein may be used in the production of polyacrylonitrile. Thus, in certain aspects, provided is a method, comprising: producing a compound of formula (3) according to any of the methods herein; and polymerizing the compound of formula (3). In one variation, provided is a method of producing polyacrylonitrile, comprising: producing acrylonitrile according to any of the methods herein; and polymerizing the acrylonitrile to produce polyacrylonitrile. The polyacrylonitrile may be suitable for various uses, including carbon fibers, in other aspects, acrylonitrile produced according to the methods described herein or producing in the systems described herein may be used in the production of acrylic acid and/or acrylamide.

EXAMPLES

The following Examples are merely illustrative and are not meant to limit any aspects of the present disclosure in any way.

Example 1 Synthesis of 3-Hydroxypropanamide (3-HPA)

This example demonstrates a process for the synthesis of 3-hydroxypropanamide (3-HPA) by combining a mixed feed stream comprising beta-propiolactone (BPL) and tetrahydrofuran (THF) with anhydrous ammonia.

Method: A 100 mL pressure vessel in a −78° C. acetone/dry ice bath was charged with 30 mL of anhydrous ammonia, fed from a 1 L anhydrous ammonia bottle through a stainless steel line, and a magnetic stir bar. A solution of BPL in THF (20 wt % by GC analysis), was introduced over 15 minutes. The pressure tube was sealed. The solution was stirred at −78° C. for 10 minutes, then warmed to 0-3° C. over the course of 10 minutes and stirred for 2 hours at that temperature. After which time, the solution was cooled down to −78° C. and the pressure top was opened, and the vessel was allowed to warm, allowing the ammonia to off-gas from −30 to 3 □C. After 50 minutes, no evolution of ammonia gas was seen, along with Insoluble, white 3-HPA on the sides of the vessel. The purple THF phase was decanted and sent for GG analysis. After GC analysis confirmed the complete conversion of BPL, the residual product was dissolved in ethanol and concentrated under vacuum to yield solid product.

Results: The results are provided in Table 1 below, referring to experiment 2. Table 1 also provides results for an experiment involving the use of BPL and aqueous ammonia at the conditions stated for experiment 1 in the table. The final composition was determined by 1H NMR.

TABLE 1

| Feed | 3-HPA | B-alanine | oligomer | Temperature ° C. |
|---|---|---|---|---|
| BPL + NH$_3$ + H$_2$O (Aqueous) | 82% | 8% | 10% | Room Temperature Add |
| BPL (20% w/w in THF NH$_3$ Anhydrous | 66% | Trace | 33% | Add at 78 warmed to −30, held at 2 for 1 hour |

Beta-Alanine not detected in second run, when BPL in THF is added dropwise to liquid ammonia.

When 3-HPA was synthesized using the conditions described above (experiment 2), only trace amounts of beta-alanine were unexpectedly observed in the product mixture, in other words, there was improved regioselectivity favoring the 3-HPA ring opening product. In comparison, when 3-HPA was synthesized using NH$_3$ H$_2$O (experiment 1), 8% of beta-alanine was observed in the product mixture.

Example 2 Synthesis of Acrylonitrile Using a Solution of 3-Hydroxypropanamide (3-HPA)

This example demonstrates a process for the synthesis of acrylonitrile by passing vaporized 3-HPA and solvent (in the presence of nitrogen carrier gas) over a dehydration agent. Method; A 50 mL stainless steel shot tank was charged with 7 g of 3-HPA, which was dissolved in 8 mL of EtOH and 20 mL of THF. This was then passed through a column of TiO$_2$ at 380-390° C. A 17:1 molar ratio of N$_2$ to 3-HPA was used, at a rate of 19 mmol of N$_2$ per minute.
Results: The results are provided in Table 2 below.

Example 3 Semi-Batch Process to Synthesize 3-Hydroxypropanamide (3-HPA)

This example studies yield and selectivity of 3-HPA when BPL feed stream is reacted with excess ammonia in liquid phase. BPL feed stream is added above and below liquid ammonia surface in the following two scenarios: (A) With no agitation in glass pressure tube and controlled addition of: carbonylation reaction permeate; permeate with lights stripped off; and distilled BPL. (B) Liquid NH$_3$ agitated using magnetic needle in glass pressure tube and controlled agitation of: carbonylation reaction permeate; permeate with lights stripped off; and distilled BPL. The yield and selectivity of 3-HPA are measured.

Example 4 Continuous Process to Synthesize Acrylonitrile (ACM)

This example studies the yield and selectivity of ACN when crude feed from Example 3 above is dehydrated through a continuous packed bed vapor phase reactor using pure TiO$_2$ or mixed TiO$_2$ and SiO$_2$ catalyst at 380-390° C. and with NH$_3$ or mixed NH$_3$ and N$_2$ carrier gas. The feed is the product of reactions A-i, A-ii, A-iii, B-i, B-ii and B-iii in Example 3 above. The temperature is 380-390° C. The carrier gas is NH$_3$ or NH$_3$+N$_2$.

Several baseline experiments are performed using a stream of NH$_3$ and H$_2$O (10 wt % water), a stream of NH$_3$, a stream of THF and H$_2$O (10 wt % water), and a stream of THF through the packed bed reactor to ascertain effect of catalyst and operating conditions on carrier fluids. The yield and selectivity of ACN, as well as the weighted hourly space velocity (WHSV) are measured.

Example 5 Continuous Process to Synthesize 3-HPA Followed by Continuous Conversion to ACN This example studies the yield and selectivity of 3-HPA and ACN when BPL feed stream is reacted with excess ammonia in vapor phase. An exemplary setup for this example is provided in FIG. 5. BPL feed stream may be atomized and fed to a reactor with a counter-current flow of NH$_3$ gas. A gas-liquid reaction may occur on an inert packed

TABLE 2

| Feed | Conversion % | ACN % | Acrylamide % | Oligomer % | Mass Balance % |
|---|---|---|---|---|---|
| 3-HPA | 100 | 82 * | 5 ** | 13 ** | 89 |
| 3-HPA + ethanol + tetrahydrofuran | 60 | 34 ** | 10 ** | 16 ** | 95 |

\* ACN isolated yield for Experiment 1.
\*\* ACN yield estimated by 1 H NMR for Experiment 2.
\*\* Acrylamide and Oligomer weight percent estimated by 1 H NMR.

bed. Unreacted NH₃ and volatiles from the BPL feed stream may be removed from the fop while product may be withdrawn at the bottom of the reactor. Phase changes and volumetric flows are determined by reactor operating temperature and pressure. The product of liquid 3-HPA is then continuously fed to a second reactor, where it is converted to acrylonitrile. The yield and selectivity of 3-HPA and ACN are measured.

Example 6 Synthesis of 3-Hydroxypropanamide (3-HPA)

This example demonstrates a process for the synthesis of 3-hydroxypropanamide (3-HPA) by combining a mixed feed stream comprising beta-propiolactone (BPL) and tetrahydrofuran (THF) and carbonylation catalyst with aqueous ammonia. Method: A 100 ml, pressure vessel was charged with aqueous ammonia at room temperature and a magnetic stir bar. A solution of bPL in THF containing carbonylation catalyst (22 wt % by GC analysis, directly from carbonylation process), was introduced slowly over 8 minutes. The solution was stirred for 2 hours at that temperature. After winch time, the stirring was stopped, and the two layers allowed to separate. The THF phase was decanted and sent for GC analysis, which confirmed complete conversion of bPL. The aqueous layer was evaporated under heat and reduced pressure to provide solid product. The feed was bPL (22% w/w in tetrahydrofuran with carbonylation catalyst), ammonia and water. The composition was analyzed by 1H NMR to have 79 percent HPA 11 percent B-alanine and 10 percent oligomer.

Example 7 Synthesis of Acrylamide Using 3-Hydroxypropanamide (3-HPA)

This example demonstrates a process for the synthesis of acrylonitrile by passing vaporized 3-HPA and solvent (in the presence of nitrogen carrier gas) over a dehydration agent. Method: A 50 ml stainless steel shot tank was charged with 16.7 g of 3-HPA. This was then passed through a column of SiO₂ at 300° C. A 15:1 molar ratio of N₂ to 3-HPA was used, at a rate of 19 mmol of N₂ per minute. The conversion was 100 percent by weight. The product was analyzed by 1H NMR to contain 99 percent acrylamide and 1 percent oligomers.

EMBODIMENTS

1. A method of producing a compound of formula (3-I) and/or a compound of formula (3):

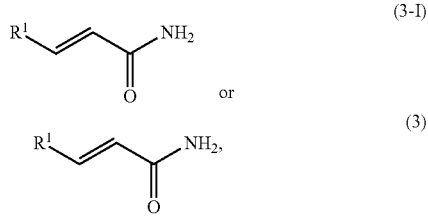

or isomers thereof, wherein $R^1$ is H or alkyl, the method comprising: combining a hydroxypropanamide stream comprising a compound of formula (2), solvent and ammonia, with dehydration agent to produce a product stream comprising the compound of formula (3-I) and/or the compound of formula (3), or isomers thereof, solvent, and ammonia, wherein: the compound of formula (2) is

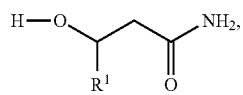

wherein $R^1$ is as defined above for formulae (3-I) and (3).
2. The method of embodiment 1, further comprising: combining a mixed feed stream comprising a compound of formula (1) and solvent, with ammonia to produce the hydroxypropanamide stream, wherein: the compound of formula (1) is

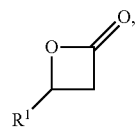

wherein $R^1$ is as defined above for formulae (3-I) and (3).
3. The method of embodiment 2, wherein the combining comprises:
providing ammonia at a temperature between −100° C. to about 35° C.; and adding the mixed feed stream to the ammonia to produce the hydroxypropanamide stream.
4. The method of embodiment 2 or 3, wherein the combining the mixed feed stream with ammonia is isothermally contrasted.
5. The method of any one of embodiments 2 to 4, further comprising: carbonylating epoxide with carbon monoxide in the presence of carbonylation catalyst and the solvent to produce the mixed feed stream.
6. The method of any one of embodiments 2 to 4, further comprising: carbonylating epoxide with carbon monoxide in the presence of a carbonylation catalyst and the solvent to produce a carbonylation product stream comprising the compound of formula (1), the solvent, and the carbonylation catalyst; and separating the carbonylation catalyst from the carbonylation product stream to produce the mixed feed stream.
7. The method of any one of embodiments 1 to 6, further comprising: distilling the product stream to isolate one or more of: the compound of formula (3-I) and/or the compound of formula (3), or isomers thereof; the solvent; and ammonia.
8. The method of any one of embodiments 1 to 7, wherein the hydroxypropanamide stream comprises molten compound of formula (2).
9. The method of any one of embodiments 1 to 7, wherein the hydroxypropanamide stream comprises molten compound of formula (2) and carrier gas.
10. The method of embodiment 9, wherein the dehydration agent is heterogeneous, and the hydroxypropanamide stream is contacted over the heterogeneous dehydration agent to produce the product stream.
11. The method of any one of embodiments 1 to 10, wherein the solvent comprises polar aprotic solvent, alcohol, or a combination thereof.
12. The method of any one of embodiments 1 to 11, wherein the solvent is vaporized.
13. A method of producing a polymer, comprising: producing a compound of formula (3-I) and/or a compound of formula (3), or isomers thereof, according to the method of any one of embodiments 1 to 12; and polymerizing the compound of formula (3-I) and/or the compound of formula (3), or isomers thereof.

14. A method of producing a hydroxypropanamide stream comprising a compound of formula (2), solvent and ammonia, wherein the compound of formula (2) is:

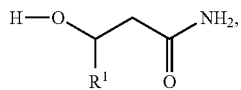
(2)

wherein R¹ is H or alkyl; the method comprising:

combining a mixed feed stream comprising a compound of formula (1) and solvent with ammonia to produce the hydroxypropanamide stream, wherein: the compound of formula (1)

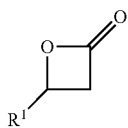

and R¹ is the same as for formula (2).

15. A method of producing a compound of formula (2):

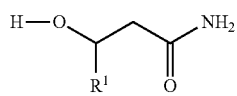

(2), wherein R¹ is H or alkyl, the method comprising:

combining a compound of formula (1) with anhydrous ammonia at a temperature between −100° C. and 35° C. to produce the compound of formula (2), wherein:

the compound of formula (1) is

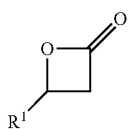

wherein R¹ is as defined above for formula (2)

16. A method of producing a compound of formula (2):

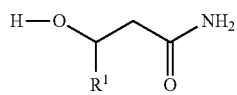

(2), wherein R¹ is H or alkyl, the method comprising:

combining a mixed feed stream comprising a compound of formula (1) and a solvent, with anhydrous ammonia at a temperature between −100° C. and 35° C. to produce a hydroxypropanamide stream comprising the compound of formula (2), wherein: the compound of formula (1) is,

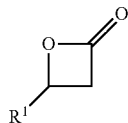

wherein R¹ is as defined above for formula (2),

17. The method of embodiment 16,
the compound of formula (1) in solvent.
the mixed feed stream comprises a 20 wt % solution of 18. The method of embodiment 16 or 17, wherein the compound of formula (2) is produced with a selectivity of greater than 50%.

19. The method of any one of embodiments 16 to 18, wherein the hydroxypropanamide stream further comprises additional products selected from the group consisting of a compound of formula (2-I), oligomer, and a combination thereof, wherein the compound of formula (2-I) is:

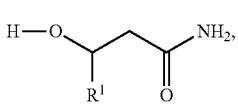
(2-I)

wherein R¹ is as defined above for formula (3), and wherein the hydroxypropanamide stream has a molar ratio of the compound of formula (2) to the additional products of 10:1.

20. The method of any one of embodiments 16 to 19, wherein the mixed feed stream and anhydrous ammonia are further combined with a base.

21. The method of embodiment 20, wherein the hydroxypropanamide stream further comprises the base, and the method further comprises: removing the base from the hydroxypropanamide stream.

22. A method of producing a compound of formula (3-I) and/or a compound of formula (3): (3-I) or (3),

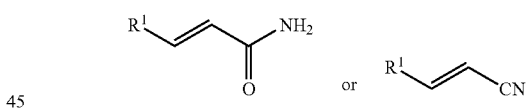

or isomers thereof, wherein R¹ is H or alkyl, the method comprising: contacting a hydroxypropanamide stream comprising molten compound of formula (2) and carrier gas over a heterogeneous dehydration agent to produce a product stream comprising the compound of formula (3-I) and/or the compound of formula (3), or isomers thereof, and optionally solvent, wherein:

the compound of formula (2) is

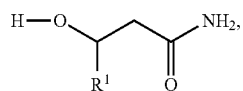

wherein R¹ is as defined above for formulae (3-I) and (3).

23. The method of embodiment 22, wherein the hydroxypropanamide stream further comprises ammonia.

24. The method of embodiment 23, wherein the carrier gas comprises nitrogen and ammonia, and wherein the relative volume of ammonia gas ranges from about 1% to about 99% with respect to the nitrogen gas, 25. The method of any one of embodiments 22 to 24, wherein the hydroxypropanamide stream further comprises vaporized solvent.

26. The method of any one of embodiments 22 to 24, wherein the hydroxypropanamide stream is further combined with vaporized solvent.

27. The method of embodiment 25 or 28, wherein the solvent comprises polar solvent.

28. The method of embodiment 25 or 28, wherein the solvent comprises ether.

29. The method of embodiment 25 or 28, wherein the solvent comprises tetrahydrofuran.

30. The method of embodiment 25 or 26, wherein the solvent comprises alcohol,

31. The method of any one of embodiment 25 to 29, wherein the solvent further comprises alcohol.

32. The method of embodiment 30 or 31, wherein the alcohol is $C_1$-$C_{10}$ alcohol.

33. The method of any one of embodiments 22 to 32, wherein the dehydration agent comprises $TiO_2$ or $SiO_2$, or a combination thereof.

34. The method of embodiment 33, wherein the dehydration agent comprises $TiO_2$ and $SiO_2$.

35. The method of embodiment 34, wherein the dehydration agent is provided in a column, and wherein the column has a zone comprising the $TiO_2$, and separately, a zone comprising the $SiO_2$.

36. The method of embodiment 35, wherein the zone comprising the $TiO_2$ operates at a first temperature, and the zone comprising the $SiO_2$ operates at a second temperature, wherein the first temperature and second temperature are different.

37. The method of embodiment 38, wherein the first temperature is higher than the second temperature.

38. A method of producing a compound of formula (3-I) and/or a compound of formula (3)

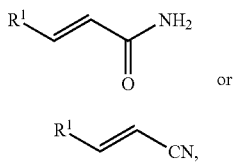

or isomers thereof, wherein $R^1$ is H or alkyl, the method comprising:
combining a mixed feed stream comprising a compound of formula (1) and a solvent, with ammonia and a dehydration agent to produce a product stream comprising the compound of formula (3-I) and/or the compound of formula (3), or isomers thereof, the solvent, and ammonia, wherein: the compound of formula (1) is

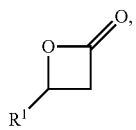

wherein $R^1$ is as defined above for formulae (3-I) and (3).

39. A system, comprising: a reactor, comprising:
at least one inlet configured to receive (i) a mixed feed stream comprising a compound of formula (1) and solvent, wherein: the compound of formula (1) is

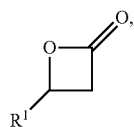

wherein $R^1$ is H or alkyl;
and (ii) ammonia; and
an outlet configured to release a hydroxypropanamide stream comprising a compound of formula (2), solvent, and ammonia, wherein: the compound of formula (2) is:

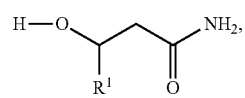

wherein $R^1$ is as defined above for formula (1),

40. The system of embodiment 39, wherein the reactor is configured to add the mixed feed stream to an excess of ammonia.

41. The system of embodiment 39 or 40, wherein the reactor is configured to add the mixed feed stream to the ammonia at a rate suitable for maintaining the temperature.

42. The system of any one of embodiments 39 to 41, wherein the reactor is configured to receive the ammonia and the mixed feed stream in liquid form.

43. The system of any one of embodiments 39 to 42, wherein the hydroxypropanamide stream is homogeneous.

44. The system of any one of embodiments 39 to 43, wherein the at least one inlet is configured to receive base.

45. The system of any one of embodiments 39 to 44, further comprising: an additional reactor configured to receive the hydroxypropanamide stream and to produce a product stream in the presence of dehydration agent, wherein the product stream comprises a compound of formula (3-I) and/or a compound of formula (3), or isomers thereof, the solvent, and ammonia, wherein: the compound of formula (3-I) and/or a compound of formula (3) are

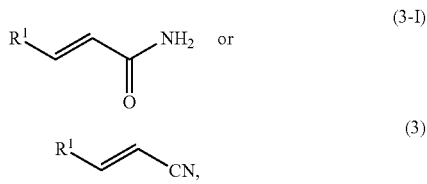

wherein $R^1$ is as defined above for formula (1).

46. The system of embodiment 45, wherein the additional reactor further comprises a multi-temperature stage column.

47. The system of embodiment 45 or 46, wherein the additional reactor Is further configured to receive a carrier gas, 48. The system of any one of embodiments 45 to 47, further comprising a distillation unit configured to collect:
i) the compound of formula (3-I) and/or the compound of formula (3), wherein: the compound of formula (3-I) and/or the compound of formula (3) are

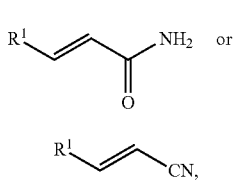

wherein $R^1$ is as defined above for formula ii) the solvent; or ammonia; or any combination of the above i)-iii).

49. The system of embodiment 48, wherein the distillation unit is further configured to collect the base, the carrier gas, or a combination thereof.

50. The system of any one of embodiments 39 to 49, further comprising: a carbonylation reactor configured to receive epoxide and carbon monoxide, and to produce a carbonylation produce stream in the presence of carbonylation catalyst and the solvent, wherein the carbonylation product stream comprises the compound of formula (1), solvent and carbonylation catalyst; and a separation unit configured to receive the carbonylation product stream and to separate at least a portion of the carbonylation catalyst to produce the mixed feed stream, 51. The system of any one of embodiments 39 to 49, further comprising: a carbonylation reactor configured to receive epoxide and carbon monoxide, and to produce a mixed feed stream in the presence of heterogeneous carbonylation catalyst and the solvent, wherein the mixed feed stream comprises the compound of formula (1) and solvent.

52. A system, comprising: a reactor configured to produce a product stream in the presence of dehydration agent, wherein the reactor comprises: an inlet configured to receive a hydroxypropanamide stream comprising a compound of formula (2), solvent, and ammonia, wherein: the compound of formula (2) is:

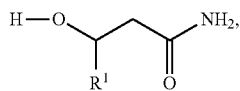

wherein $R^1$ is H or alkyl; and an outlet configured to output the product stream, wherein the product stream comprises a compound of formula (3-I) and/or a compound of formula (3), or isomers thereof, the solvent, and ammonia, wherein: the compound of formula (3-I) and/or the compound of formula (3) are

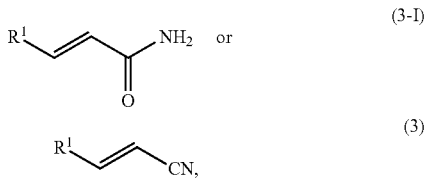

wherein $R^1$ is as defined above for formula (2).

53. A system, comprising: a reactor configured to produce a product stream in the presence of dehydration agent, wherein the reactor comprises: at least one inlet configured to receive (i) a mixed feed stream comprising a compound of formula (1) and solvent, wherein: the compound of formula (1) is

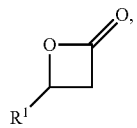

wherein $R^1$ is H or alkyl; and (ii) ammonia; and an outlet configured to output the product stream, wherein the product stream comprises a compound of formula (3-I) and/or a compound of formula (3), or isomers thereof, the solvent, and ammonia, wherein: the compound of formula (3-I) and/or a compound of formula (3) are

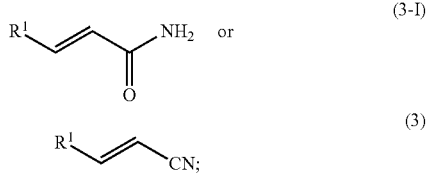

wherein $R^1$ is as defined above for formula (1).

54. The system of embodiment 53, wherein the reactor is configured to add the mixed feed stream to an excess of ammonia.

55. The system of embodiment 53 or 54, wherein the reactor is configured to add the mixed feed stream to the ammonia at a rate suitable for maintaining the temperature.

56. The system of any one of embodiments 53 to 55, wherein the reactor is configured to receive the ammonia and the mixed feed stream in liquid form.

57. The system of any one of embodiments 53 to 56, wherein the at least one inlet is configured to receive base.

58. The system of any one of embodiments 53 to 57, wherein the reactor further comprises a multi-temperature stage column.

59. The system of any one of embodiments 53 to 58, wherein the reactor is configured to receive a carrier gas.

60. The system of any one of embodiments 53 to 59, further comprising a distillation unit configured to collect:

i) the compound of formula (3-I) and/or the compound of formula (3), wherein: the compound of formula (3-I); and/or the compound of formula (3) are wherein $R^1$ is as defined above.

ii) the solvent; or iii) ammonia; or any combination of the above i)-iii).

61. The system of embodiment 60, wherein the distillation unit is configured to collect the base, the carrier gas, or a combination thereof.

The invention claimed is:

1. A method comprising:
combining a beta-hydroxy amide stream comprising a beta-hydroxy amide with a dehydration agent to produce a product stream comprising an unsaturated amide and/or an unsaturated nitrile, wherein the beta-hydroxy amide stream comprises molten beta- hydroxy amide.

2. The method of claim 1 wherein the beta- hydroxy amide is combined with the dehydration agent in the presence of a solvent and ammonia.

3. The method of claim 1 comprising preparing the beta-hydroxy amide stream by combining a beta lactone with ammonia.

4. The method of claim 3 comprising adding the ammonia to the beta lactone at a temperature of about −100° C. to less than 100° C.

5. The method of claim 3 wherein the combining of the beta lactone with ammonia is isothermally controlled.

6. The method of claim 3 comprising contacting carbon monoxide with an epoxide in the presence of a carbonylation catalyst to prepare the beta lactone.

7. The method of claim 1 comprising distilling the product stream comprising the unsaturated amide and/or the unsaturated nitrile to isolate the unsaturated amide and/or the unsaturated nitrile.

8. The method of claim 6 wherein:
the beta lactone corresponds to formula (1),

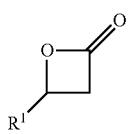

(1)

the beta-hydroxy amide corresponds to formula (2),

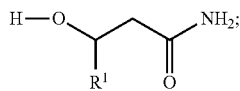

(2)

and,
the unsaturated nitrile corresponds to formula (3),

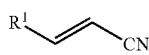

(3)

the unsaturated amide corresponds to formula (3-I),

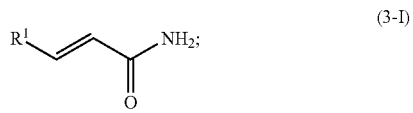

(3-I)

and,
the epoxide corresponds to formula (E),

(E)

wherein $R^1$ is H, alkyl, alkenyl, cycloalkyl, or aryl.

9. The method of claim 7 wherein the beta- hydroxy amide stream comprises molten beta-hydroxy amide and a carrier gas.

10. The method of claim 3 wherein the dehydration agent is heterogeneous, and the beta-hydroxy amide stream is contacted with the heterogeneous dehydration agent to produce the product stream comprising the unsaturated amide and/or the unsaturated nitrile.

11. The method of claim 3, comprising performing one or more of the steps in the solvent of a polar aprotic solvent, an alcohol, or a combination thereof.

12. The method of claim 3 comprising contacting the beta lactone with anhydrous ammonia at a temperature of from −100° C. to 35° C. to prepare the beta-hydroxy amide.

13. The method of claim 12 contacting the beta lactone and the anhydrous ammonia in a solvent.

14. The method of claim 12 wherein the beta lactone and the anhydrous ammonia are contacted in the presence of a base.

15. The method of claim 1 wherein the dehydration agent comprises $TiO_2$ or $SiO_2$, or a combination thereof.

16. The method of claim 1 wherein the dehydration agent comprises $TiO_2$ and $SiO_2$.

17. The method of claim 16, wherein the dehydration agent is provided in a column, and wherein the column has a zone comprising the $TiO_2$ and a separate zone comprising the $SiO_2$.

18. The method of claim 17, wherein the zone comprising the $TiO_2$ operates at a first temperature, and the zone comprising the $SiO_2$ operates at a second temperature, wherein the first temperature and second temperature are different.

19. A method comprising:
preparing an unsaturated amide or unsaturated nitrile according to claim 1 and polymerizing the unsaturated amide or unsaturated nitrile.

20. The method of claim 1, wherein the beta-hydroxy amide is hydroxypropanamide.

* * * * *